(12) United States Patent
Leu et al.

(10) Patent No.: US 8,087,579 B2
(45) Date of Patent: *Jan. 3, 2012

(54) SYSTEMS AND METHODS FOR VERIFYING BRANDING OF PHARMACEUTICAL/MEDICAL CONTAINERS

(75) Inventors: Chih-Jen Leu, East Brunswick, NJ (US); James G. McErlean, Uniondale, PA (US); Dennis Wayne Rice, Flanders, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/951,692

(22) Filed: Nov. 22, 2010

(65) Prior Publication Data

US 2011/0120062 A1  May 26, 2011

Related U.S. Application Data

(63) Continuation of application No. 11/950,617, filed on Dec. 5, 2007, now Pat. No. 7,837,093, which is a continuation of application No. 11/873,959, filed on Oct. 17, 2007, now Pat. No. 7,770,364.

(60) Provisional application No. 60/852,737, filed on Oct. 19, 2006, provisional application No. 60/874,340, filed on Dec. 12, 2006.

(51) Int. Cl.
*G06F 17/00* (2006.01)
(52) U.S. Cl. .............. 235/375; 705/3; 221/13; 221/256; 221/310; 700/216
(58) Field of Classification Search .................. 235/375; 705/3; 221/13, 256, 310; 700/216
See application file for complete search history.

(56) References Cited

U.S. PATENT DOCUMENTS

2003/0176942 A1 * 9/2003 Sleep et al. .................... 700/213
* cited by examiner

*Primary Examiner* — Allyson Trail
(74) *Attorney, Agent, or Firm* — Stroock & Stroock & Lavan LLP

(57) ABSTRACT

Systems and methods for verifying branding of pharmaceutical/medical containers are provided. In some embodiments, systems for verifying branding of at least one medication container associated with at least one of a prescription and medication order are provided. The systems including: a scanning system including at least one scanner for determining the branding of at least one of a first medication container and a cap used to cover the first medication container; a transport system that transports the first medication container; and a control system that: controls the transport system to transport the first medication container to the scanning system; and controls the scanning system to determine whether the branding of at least one of the first medication container and the cap correctly matches a predetermined branding among a plurality of brandings based on predetermined criteria.

23 Claims, 34 Drawing Sheets

SYSTEMS AND METHODS FOR VERIFYING BRANDING OF PHARMACEUTICAL/MEDICAL CONTAINERS

CROSS-REFERENCE TO RELATED APPLICATION

This application is a continuation of U.S. patent application Ser. No. 11/950,617, filed Dec. 5, 2007, now U.S. Pat. No. 7,837,093, which is a continuation of U.S. patent application Ser. No. 11/873,959, filed Oct. 17, 2007, now U.S. Pat. No. 7,770,364, which claims the benefit of U.S. Provisional Patent Application No. 60/852,737, filed Oct. 19, 2006 and U.S. Provisional Patent Application No. 60/874,340, filed Dec. 12, 2006, the entire content of which are expressly incorporated herein by reference thereto.

This application also claims the benefit under 35 U.S.C. §119(e) of U.S. Provisional Patent Application No. 60/874,340, filed Dec. 12, 2006, which is hereby incorporated by reference herein in its entirety.

This application is related to U.S. patent application Ser. No. 11/873,953, filed Oct. 17, 2007 and U.S. patent application Ser. No. 12/952,674, filed Dec. 4, 2007 and titled SYSTEMS AND METHODS FOR PERFORMING QUALITY ASSURANCE OF BRANDING OF PHARMACEUTICAL/MEDICAL CONTAINERS AND COMPUTER ASSISTED SYSTEMS AND METHODS FOR BRANDING PHARMACEUTICAL/MEDICAL CONTAINERS, each of which is hereby incorporated by reference herein in its entirety.

TECHNICAL FIELD

The disclosed subject matter relates generally to systems and methods for verifying branding of pharmaceutical/medical containers.

BACKGROUND

In mail service pharmacies and large retail pharmacies, prescription drugs are dispensed in high volume. For such services, automatic pill dispensing systems can be used to dispense prescription drugs and label pill containers. The containers can then be provided to a patient for whom the prescription was written.

Automatic pill dispensing systems can require a large infrastructure and a health care entity that provides prescriptions to patients may desire to contract out the filling of prescriptions. Accordingly, the entity hired to fill these prescriptions, such as pharmacy or pharmacy benefits management (PBM) entity may need to fill various prescriptions for multiple health care entities and may therefore need to brand the various prescriptions differently.

A known automatic pill dispensing system 100 is described in U.S. Pat. No. 5,771,657, which is hereby incorporated herein by reference in its entirety. In the U.S. Pat. No. 5,771,657 patent, as shown in FIG. 1, orders (e.g., orders to fill prescriptions) are received by a host computer 9 which forwards the orders to a distributed computer system that can include a central computer called a Pharmacy Automation Controller 10 (PAC). PAC 10 maintains an order file of the information about each prescription to be filled that can include information needed to fill each prescription. The order file can, for example, be used to prepare a prescription label for each bottle/container (hereinafter bottle). The order file can also be used to facilitate printing literature that can be placed in a shipping container with the bottle(s). PAC 10 can also update the order file to maintain a record of the current status of each prescription being filled as it progresses through the automated system.

PAC 10 can control a set of Print, Apply and Load (PAL) stations 14 which print prescription bottle labels, apply the labels to bottles, and load the labeled bottles onto bottle carriers that preferably receive the bottles in scheduled locations. PAC 10 can also control a carrier conveyer system 21 that carries the bottle carriers to different parts of system 100, and one or more automatic drug dispensing machines 23 that dispense tablets and/or capsules into the bottles in the bottle carriers as they are carried by conveyer system 21. In addition, PAC 10 controls bottle cappers 25 that apply caps to the bottles, and OCP (order consolidation and packaging) stations 29 that unload bottles from the carriers and place them in shipping containers corresponding to a patient order. Further, PAC 10 can control literature printers 31 which print literature, for each prescription order, that can be enclosed in an envelope. Finally, PAC 10 can utilize bar code data that identifies the prescription order. The bar code can show through a window in the envelope. Envelopes can be placed on a literature conveyer 34 which carries the envelopes from the literature printers 31 to the OCP stations 29.

Conveyer system 21 carries the bottles in the carriers from PAL stations 14 through the automatic drug dispensing machines 23 to bottle cappers 25, and then from bottle cappers to OCP stations 29. Conveyer system 21 also carries empty carriers back to PAL stations 14. From bottle cappers 25, conveyers 56 feed the carriers onto an endless conveyer loop 71 which transports, for example, four carriers of a rank to one of, say, six OCP stations 29. Other numbers of OCP stations 29 can also be utilized. OCP stations 29 each also have a literature dispensing mechanism, which inserts the printed literature into each shipping container with the filled and capped prescription bottles.

As shown in FIG. 2, bottles to be automatically filled with the prescription drugs are introduced to the automated system by hoppers 37, which receive the bottles in bulk form and automatically feed the bottles to unscramblers 39. In one embodiment, one of the hoppers 37 and one of the unscramblers 39 can be for large bottles (e.g., 160 cc), and the remaining hoppers and unscramblers can be for small bottles (e.g., 110 cc). The small bottle size can preferably accommodate a majority of the automatically filled prescriptions. The bottles are directed to PAL stations 14 on bottle conveyers 41 and 43, for example, one for large bottles and one for small bottles.

Conveyers 45, under control by PAC 10, carry the bottle carriers from the four PAL stations 14 to carrier buffers at the entrances of the four automatic drug dispensing machines 23 in which the tablets or capsules of the prescriptions are automatically dispensed into the prescription bottles under the control of PAC 10. Because of the organization provided by the carriers, the bottles are arranged into four columns approaching each automatic dispensing machine 23. Since there are four automatic dispensing machines 23, 16 parallel prescription bottle columns can approach the dispensing machines. In this embodiment, the four automatic drug dispensing machines each have 384 drug dispensers arranged four columns wide and 96 rows deep to provide a total of 1,536 pill dispensers. The automatic drug dispensing machines are similar to those described in the U.S. Pat. No. 5,660,305, which is hereby incorporated herein by reference in its entirety. Each dispensing lane is divided into 32 buffer assemblies, each containing twelve drug dispensers oriented six on each side of a conveyer within the dispensing machine.

The carrier will be released by PAL station 14 onto a conveyer 45 which carries the carrier loaded with the labeled empty prescription bottles to an automatic dispensing machine 23, of which there are four, one for each PAL station 14. When a carrier moves out of the last row position in a dispensing machine, all of the prescription bottles in that bottle carrier should be filled and a conveyer 56 transports the prescription bottles now filled with the prescriptions to a bottle capper 25.

Bottle quality assurance area 109 has several stations at which pharmacists can scan the bar code on the bottles and visually inspect the contents of the bottles. The scan of the bottle bar code will bring up a display on the pharmacist's terminal which preferably includes all the information regarding the particular prescription and order. Such information can include, for example, the drug name, and instructions which identify the reason for the verification. All of the bottles that pass this inspection can be inserted or reinserted by the pharmacist on a bottle stream conveyer 111 to send the inspected bottles to the BSP (bottle sorting and packaging) station 112. Conveyer 108 leads to a star wheel or other diverter mechanism 114 which, optionally under the control of a controller for BSP station 112, deposits the bottle in a bottle stream conveyer 116 leading to the bottle quality assurance area 109 or into a bottle stream conveyer 118 leading to BSP station 112.

If the literature pack is on conveyer 34, but because of failure of the bar code reader (not shown) or the literature sorting mechanism (not shown), does not get diverted at BSP station 112, conveyer 34 will carry the literature package to package quality assurance area 96 where the literature pack can be manually added to the package. If, because of a malfunction, a literature envelope is not deflected by a deflector 89 (FIG. 3), because of, for example, an improper bar code on the envelope, the envelope will continue on conveyer 34 to the end of the conveyer and be dumped into a receptacle at the package quality assurance station 96. If the bag does not contain a literature pack, then the bag is diverted into a tote (not shown) which will then be transported by a conveyer 34 to the package quality assurance station 96, where the shipping container will be assembled with the literature pack manually 137.

As shown in the OCP station 29 of FIG. 3, the four carriers of a rank are first received in a carrier buffer 75 from which they are loaded onto a turntable 77. An RFID tag reader (not shown) verifies that the correct carriers are in place on turntable 77, which selectively rotates the carriers into a position to have the bottles removed by robotic arm 79. OCP station 29 also contains equipment 91 for packing literature into shipping containers, which take the form of bags 83, along with the prescription bottles of a given order. OCP station 29 also includes a bagging machine 181 which presents the bags for successive orders to be loaded in sequence at a loading position. Bagging machine 181 can print a bar code identifying the order directly on each bag 83. The printed data may include the mailing address to which the shipping container is to be sent.

Bag 83 is shown at the loading position with its mouth open. The opening of the mouth of bag 83 can be accomplished by a blower (not shown) provided as part of bagging machine 181. Conveyer 34 brings envelopes 85 containing literature to be packed in shipping containers to OCP station 29 in the reverse sequence that the patient orders are to be packed at that OCP station 29 for a given rank of carriers. At OCP stations 29, literature conveyor 34 can be in the form of a literature sortation system of the type used in mail sortation by the U.S. Post Office. The literature sortation system can include a pair of belts 88 that pass the envelopes along from station to station. Deflector 89 can optionally be located between each pair of belts 88, and be controlled by the OCP station controller to deflect selected literature envelopes into a literature dispensing mechanism 91.

When a rank of carriers is directed to a given OCP station 29 by PAC 10 from bottle cappers 25, PAC 10 can send an unload message to the controller for the OCP station 29. The unload message can contain an indication of the sequence that the orders are to be unloaded from the rank of carriers at the station, as well as containing the information as to the scheduled position of the bottles of each order in the four carriers of the rank of carriers to be unloaded. At the same time that PAC 10 sends an unload message to the controller of the OCP station 29, it can send a corresponding autopublish message to printers 31. The message can contain the information to be printed for the complete orders contained in the rank of carriers being sent to an OCP station 29. The autopublish message will also contain the sequence in which the corresponding orders are to be unloaded at the OCP station 29. In response to the auto publish message, one of the printers 31 will print literature for the orders and deposit the literature packs for the orders on literature conveyer 34 in reverse order from that in which the orders are to be unloaded at the OCP station 29.

Each literature pack is preferably enclosed in an envelope having a die cut window through which a bar code is readable by a bar code reader 87. The bar code can be printed by an appropriate printer 31 to identify the order for which the literature pack is printed. As the envelopes containing literature packs are carried past the OCP station 29 in the literature sortation system, the bar code readable through the window in each envelope will be read by a bar code reader 87, that can verify that the bar code coincides with an order in the unload message received by the controller for OCP station 29. The controller for OCP station 29 will then cause deflector 89 to deflect the envelope into literature dispensing mechanism 91. Since the conveyor brings the literature envelopes to an OCP station 29 in the reverse sequence that the corresponding patient order is to be packed at the packing station, the envelopes will be packed into the dispensing mechanism in that sequence. When bag 83 is ready to be packed at an OCP station 29, literature dispensing mechanism 91 first inserts a literature envelope into the bag 83 where it will be positioned at one side of the bag (by, e.g., gravity). This effect is achieved by orienting the bag 83 at a slight tilted position at bagging machine 181. After the literature has been inserted, robotic arm 79 unloads the bottles of the order from the scheduled positions in the four carriers on the turntable in accordance with the unload message. Robotic arm 79 preferably includes a bar code reader so that each time a bottle is lifted out of a carrier by robotic arm 79, the label on the bottle is read and verified.

The prescription bottles are then loaded into the bag 83 by a bottle loading mechanism 93. When the shipping containers 83 have been verified and filled with a literature pack and with a patient's order, the bag is sealed and dropped onto a conveyer 95 which carries the sealed shipping container to a mailing area where the bag is read and logged and then mailed to the customer. If the bag 83 does not contain a literature pack, then the bag is diverted into a tote 99 which will then be transported by a conveyer 101 to the package quality assurance station 96 where the shipping container will be assembled with the literature pack manually.

An alternative automated prescription filling system and method with automated labeling and packaging system and method and automated order consolidation system/method in U.S. Pat. No. 6,892,512 issued to Rice et al., which is hereby incorporated herein by reference in its entirety. One embodiment of the U.S. Pat. No. 6,892,512 patent is a system that includes an order consolidation station configured to receive at least one bottle containing pills individually counted and/or at least one package containing pharmaceutical products without having been designated for any of the orders when the package was created and/or at least one literature pack optionally including patient specific information. The order consolidation station is further configured to combine automatically the received bottle and/or package and/or literature pack into a container to be sent to a recipient including, for example, mail order pharmacies, wholesalers and/or central fill dealers for subsequent distribution or sale including retailer distribution or sale. The bottle is specifically designated for the order, and the order generally includes at least one prescription for the package.

U.S. Pat. No. 7,010,899 issued to McErlean, et al., which is hereby incorporated herein by reference in its entirety, describes an alternative embodiment of a system and method of placing a printed label on a bag. A first plurality of rollers can feed one or more bags, and a second plurality of rollers can feed one or more labels. Additionally, for example, a tamp pad can place the label on the bag. As shown in FIG. 4, bagger 181 can be used with either or both of system 100 and ALPS system 250.

FIG. 5 is similar to FIG. 2, and shows exemplary aspects of the automated pill dispensing system 310 shown in FIG. 4. In operation, one or more literature packs can be printed on a printer 31, and sent to a collator 32 for collation into individual literature packs. More than one collator 32 can optionally be used. Once literature packs are collated, they can travel, for example, on a standard pinchbelt conveyor 33 to a literature pack sorter 35, where they are sorted into literature pack batches. Although two literature pack sorters 35 are shown, any number of literature pack sorters can be utilized to suit, for example, cost and/or volume considerations. On command from, for example, an OCP station 29, the literature pack batches can optionally be manually transferred from the one or more sorters 35 to a dispatch unit 36. Again, any number of dispatch units can be utilized to accommodate, for example, manufacturing, facility size and/or cost requirements or constraints. Dispatch units 36 can feed the literature packs to an OCP station 29.

Some systems, such as those illustrated in FIGS. 1-5, can also include, for example, a PAC router, between the Host Computer 9 and the PAC 10, that can divert work between various dispensing pharmacies. The PAC router can include a smart scheduler that can determine, for example, based on cost, where to route an order. The PAC router can achieve, for example, load distribution and/or matching of an order with an appropriate dispensing pharmacy.

We have determined, however, that the above systems lack the ability and have never considered the functionality of branding the bottle, package, and/or container with indicia corresponding to a plurality of parties when the dispensing systems dispense medication and/or pharmaceuticals for multiple pharmacy brands and/or multiple pharmacy health benefit plans, and the like.

SUMMARY

In some embodiments, an automated dispensing system (ADS) can receive empty containers (e.g., bottles, boxes, packages, etc). These containers can be, for example, labeled with a uniquely identifiable customer label. The labeled containers can be loaded into a carrier that caries containers. In alternative embodiments, a carrier is not required to be used to transport the containers, and any conventional transport device may be used. The carrier can be transported to and from various stations by a transport system. The container carrier can travel through, for example, a solid pharmaceutical dispensing system where all or some of the containers in the carrier can be filled with a specific quantity of pharmaceutical product. The carrier can be transported to a capping and branding station where the containers can be capped and branded. In various embodiments, the caps can be pre-branded, blank, or a combination of pre-branded and blank. Where at least some of the containers are branded with blank caps, a carrier and/or container can be transported to a branding station that can brand caps with cap labeling information (e.g., logos, graphics, artwork, text, etc.) that can be specific to each cap. A cap can be, for example, a cover, a lid, a top, a plug, a stopper, or any object used to partially or totally seal and/or close a container.

In some embodiments, the branding of a container, for example, the branding of a cap of the container and/or the branding of the body of the container can be verified and corrected if incorrect. Verification can be performed using various systems and/or methods, such as, for example, bar codes, vision systems, and/or RFID. When a bottle or carrier passes under scanners, a bar code can be read and verified. Bottles found to have incorrect branding can be, for example, corrected or rescheduled for filling and branding. If a barcode is not properly read, the bottle can be flagged for inspection, for example, by manual inspection.

In some embodiments, systems for verifying branding of at least one medication container associated with at least one of a prescription and medication order are provided. The systems including: a scanning system including at least one scanner for determining the branding of at least one of a first medication container and a cap used to cover the first medication container; a transport system that transports the first medication container; and a control system that: controls the transport system to transport the first medication container to the scanning system; and controls the scanning system to determine whether the branding of at least one of the first medication container and the cap correctly matches a predetermined branding among a plurality of brandings based on predetermined criteria.

In some embodiments, the control system further corrects the branding if it is determined that the cap covering the first medication container is not of the predetermined branding. In some embodiments, the systems further include a dispensing, capping, and branding system for dispensing, capping, and branding at least one order; and a quality assurance station for correcting the branding of at least one of the first medication container and the cap used to cover the first medication container using a computer assisted branding system, wherein the control system further: controls the transport system to transport the at least one first medication container to the quality assurance station if it is determined the quality assurance station can correct the branding; or schedules a new order for the dispensing, capping, and branding system if it is determined the quality assurance station cannot correct the branding. In some embodiments, the plurality of possible brandings include indicia describing a third party that is responsible for an order associated with the medication container that will be received by at least one member of a pharmaceutical benefits plan.

In some embodiments, methods for verifying the branding of at least one medication container associated with at least one of a prescription and medication order are provided. The methods including: transporting a first medication container to a scanning system; and scanning at least one of the first medication container and a cap used to cover the first medication container at the scanning system to determine whether a branding of at least one of the first medication container and the cap used to cover the first medication container correctly matches are determined branding among a plurality of brandings based on predetermined criteria.

In some embodiments, methods for verifying the branding of at least one medication container associated with at least one of a prescription and medication order are provided. The methods including: dispensing a medical product into a first medication container; capping the first medication container; branding the first medication container with a predetermined branding among a plurality of brandings based on predetermined criteria transporting a first medication container to a scanning system; and scanning at least one of the first medication container and a cap used to cover the first medication container at the scanning system to determine whether a branding of at least one of the first medication container and the cap used to cover the first medication container correctly matches a predetermined branding among a plurality of brandings based on predetermined criteria.

BRIEF DESCRIPTION OF THE DRAWINGS

FIG. 19 illustrates a method that can be used for cap verification in accordance with some embodiments of the disclosed subject matter.

DETAILED DESCRIPTION

Figure 1:
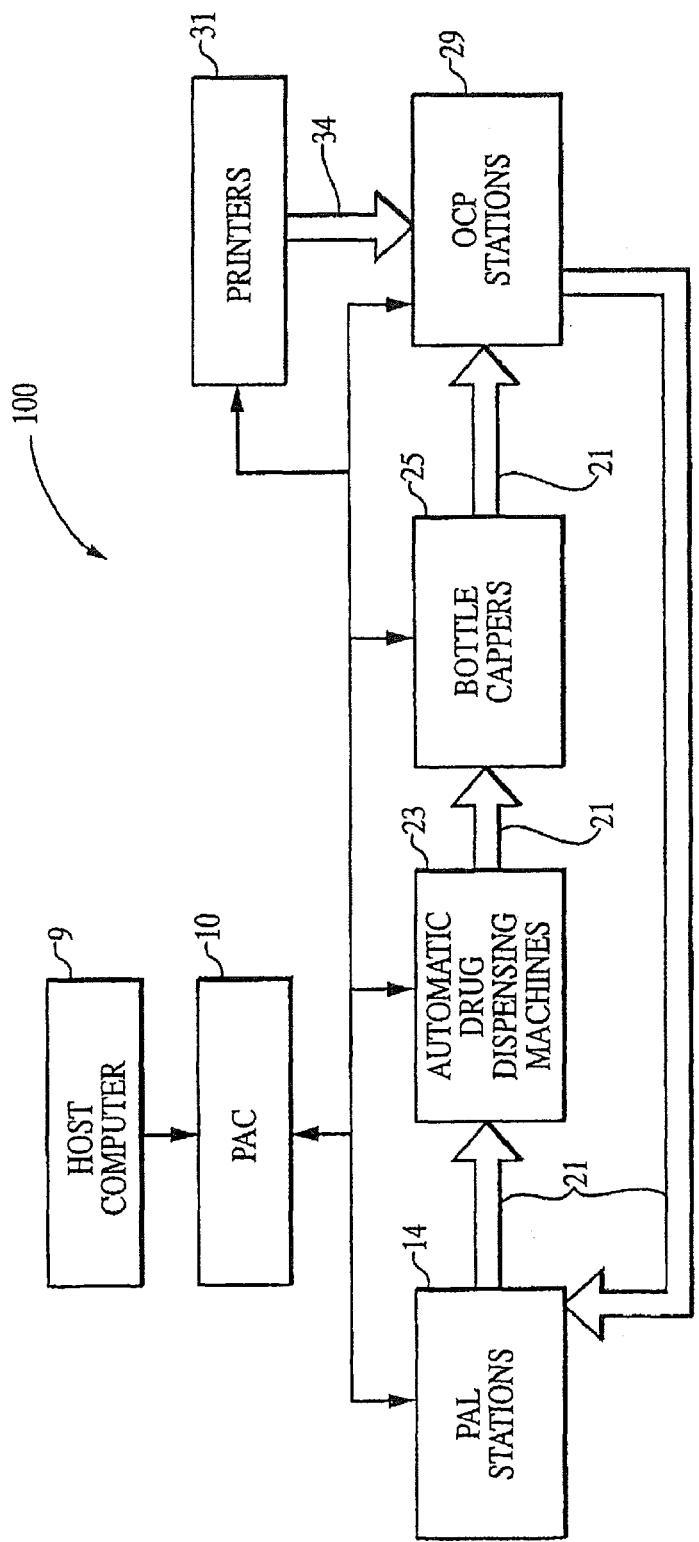
FIGS. 1-5 are diagrams illustrating automated pill dispensing systems that can use some embodiments of the disclosed subject matter.
Figure 2:
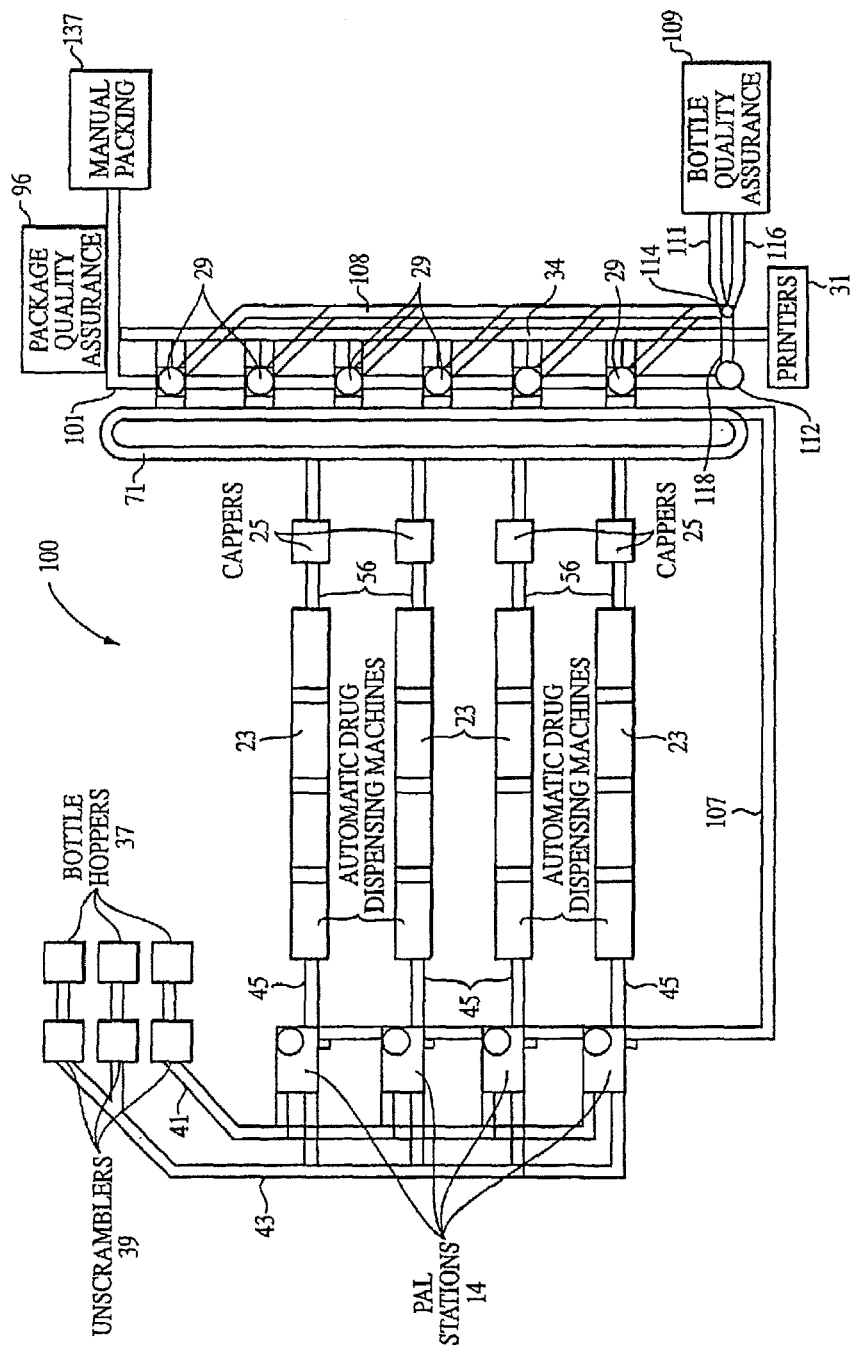
Figure 3:
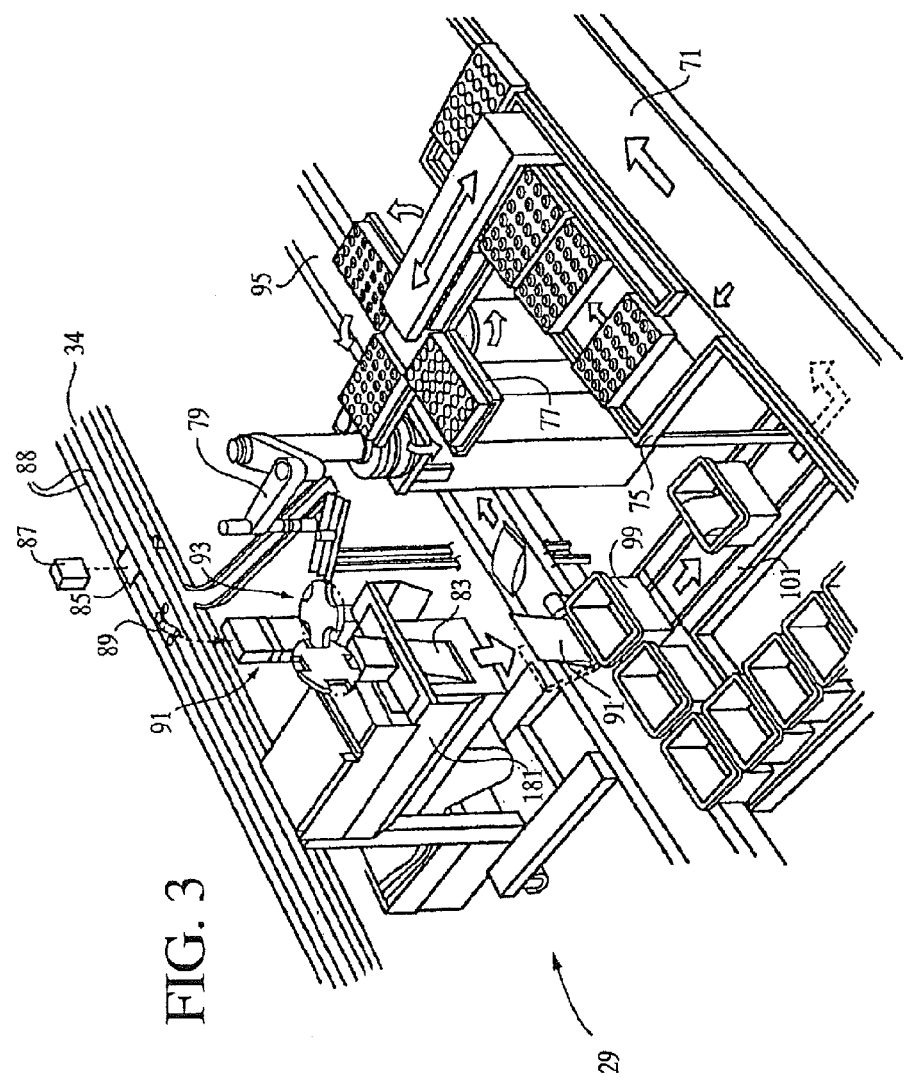
Figure 4:
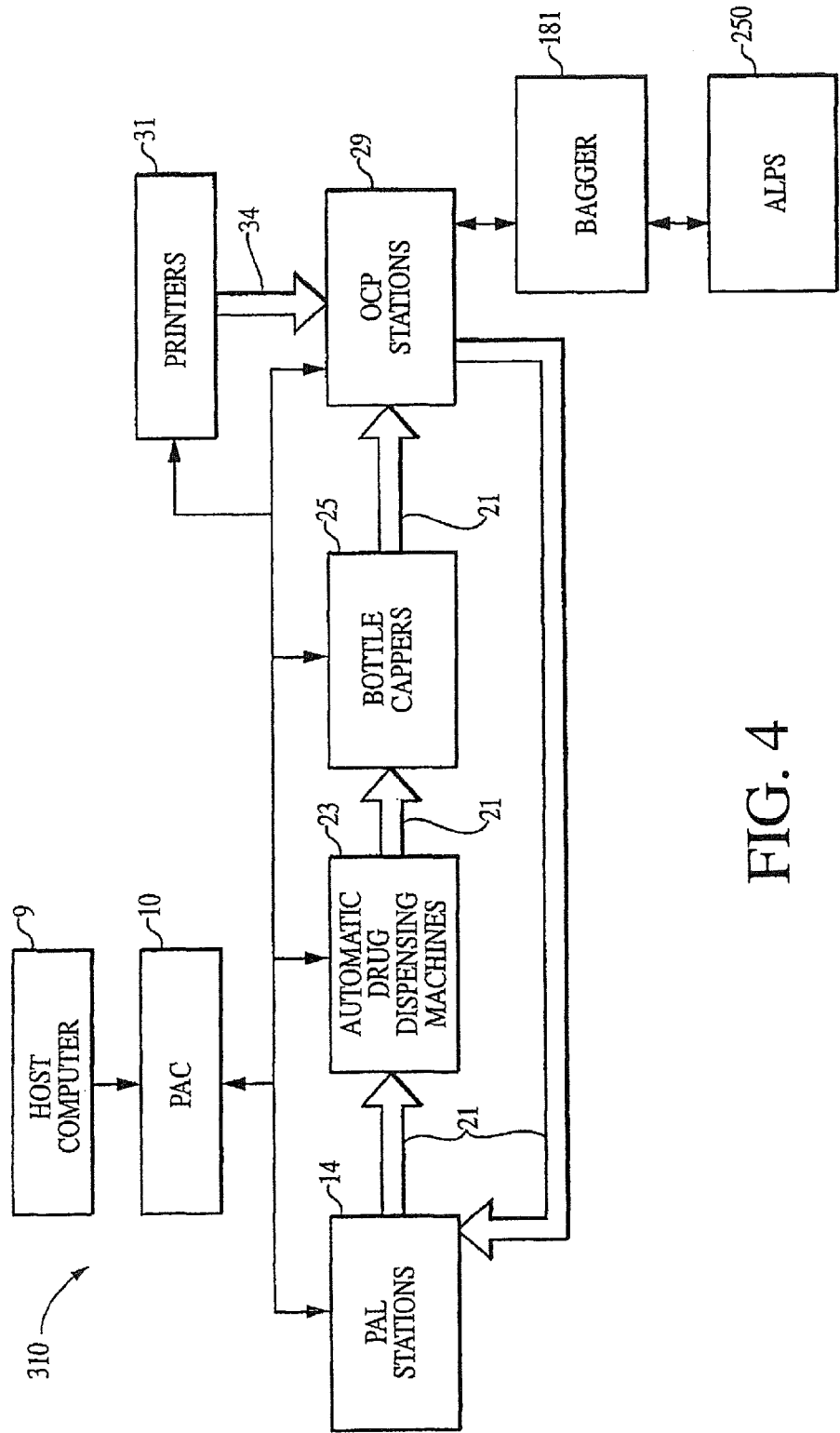
Figure 5:
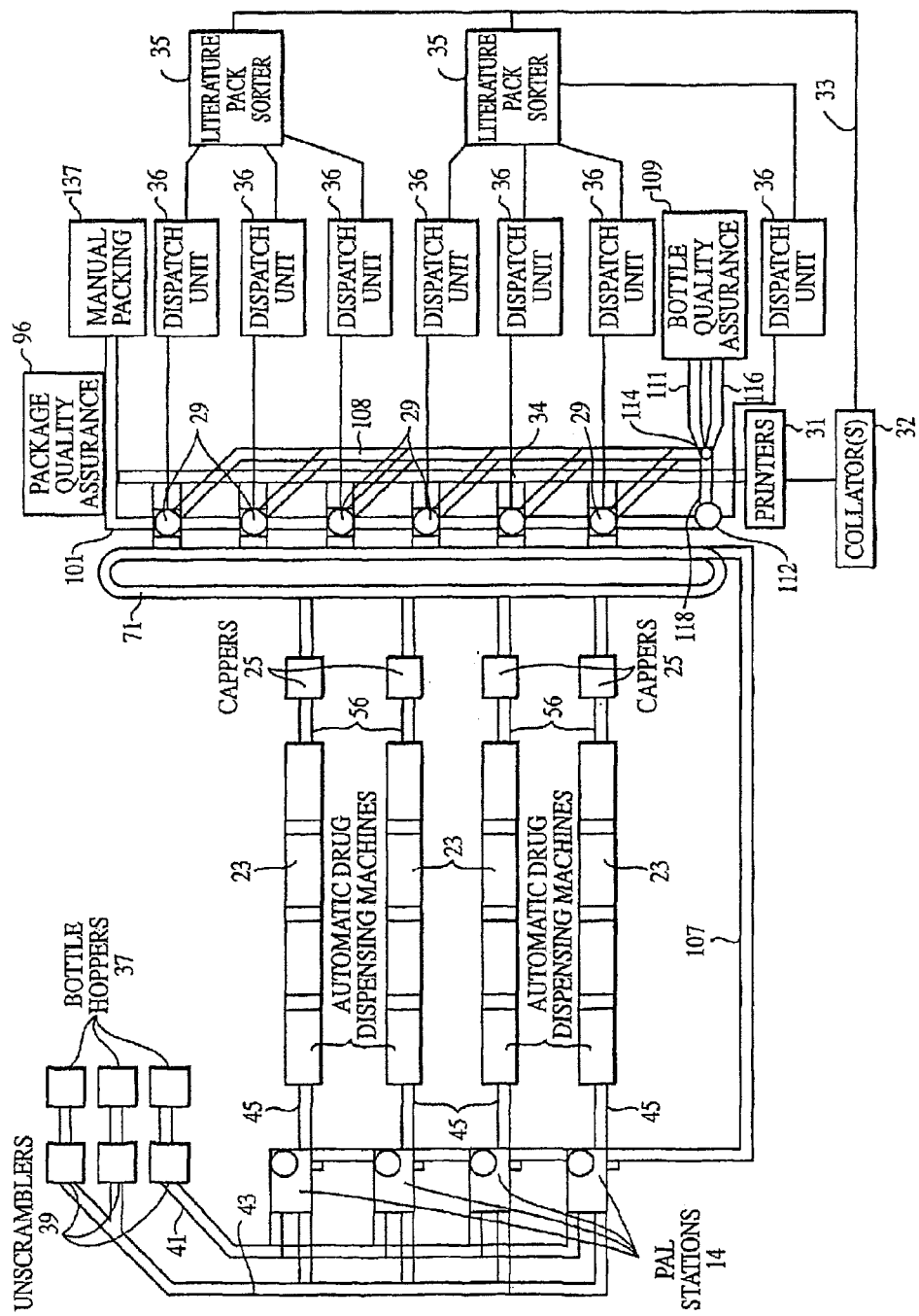

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. Other alterations or modifications of the above processes are also contemplated. For example, further insubstantial approximations of the process and/or algorithms are also considered within the scope of the processes described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

In accordance with one embodiment of the invention, we have determined that a pharmacy or other entity, such as a pharmacy benefits management (PBM) entity like the assignee of the present application, Medco Health Solutions, may desire to apply a variety of differently branded caps to bottles. This may be done, for example, to solicit new business by offering mail order prescription dispensing services to other health care entities and may include providing prescription services to hospitals, clinics, retail or chain pharmacies, international markets, prisons, etc. The customer company's brand may be prominent on all items received by the patient (prescriptions, notices, mailings, etc.), while the pharmacy name may be transparent unless, for example, it is required by regulatory agencies to be displayed.

To, for example, enable a pharmacy or PBM to fill and brand product for various third parties, some embodiments of the disclosed subject matter advantageously provide third party dispensing (3PD) systems and methods. These systems and methods can include branding systems, branding items (e.g., branding initiatives), branding methods, and verification and/or quality assurance, as described below in more detail.

In some embodiments, when a patient's doctor is called for a prescription consultation, a pharmacist may mention the 3PD name rather than then pharmacy's name. The call or contact can be taken in by, for example, branded party's 800 phone number, electronic communications, or other order method, thus identifying the branded partner. Alternatively, the order may be forwarded from the third party. Many such prescriptions, possibly for various third party entities, can be filled in accordance with some embodiments of the disclosed subject matter.

Figure 6:
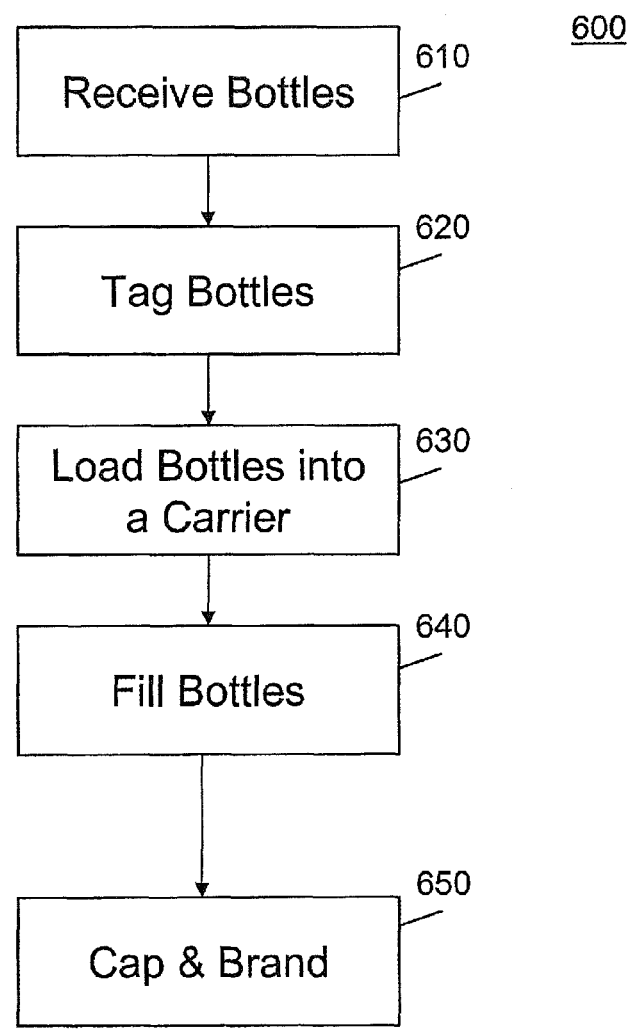
FIG. 6 illustrates a method for filling, capping, and branding a bottle in accordance with some embodiments of the disclosed subject matter.

As shown in FIG. 6, an automated dispensing system (ADS) can receive, at 610, empty bottles from, for example, a bottle unscrambling system. These bottles can be, for example, tagged, at 620, with a uniquely identifiable customer label. The labeled bottles can be loaded, at 630, into a carrier that caries bottles arranged in a grid of rows and columns. In alternative embodiments, a carrier is not required to be used to transport the bottle and/or container, and any conventional transport device may be used. The carrier can be transported to and from various stations by a transport system such as, for example, a spool driven conveyor. The carrier can have a tag, such as, for example, an intelligent recognition tag (e.g., active RFID, bar code, etc.) for identifying, tracking, and routing of the carrier. The bottle carrier can travel through, for example, a solid pharmaceutical dispensing system where all or some of the bottles in the carrier can be filled, at 640, with a specific quantity of pharmaceutical product.

Figure 6A:
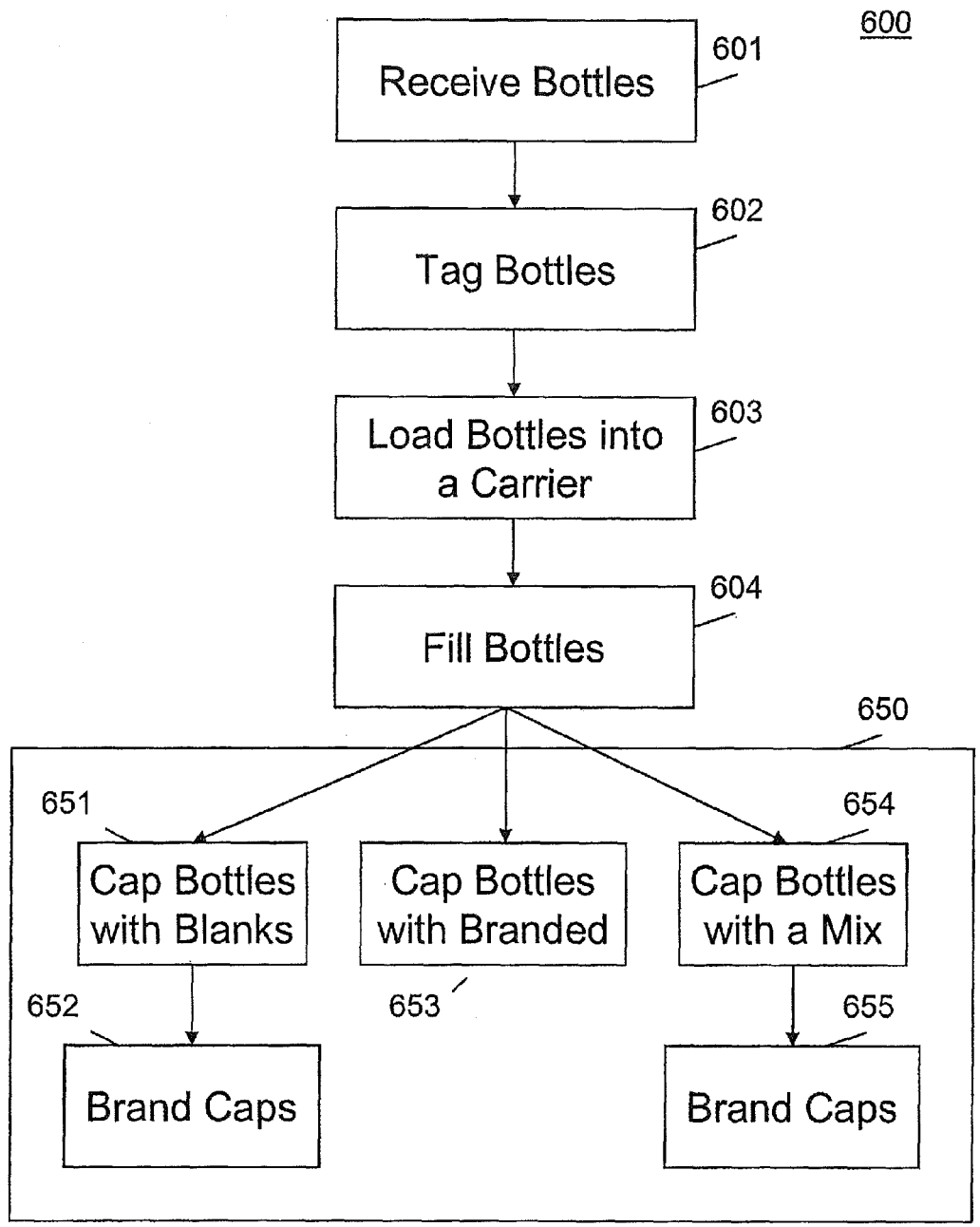
FIG. 6A illustrates various alternative methods for capping and branding illustrated in FIG. 1.

The bottle carrier can be transported to a capping and branding station where the bottles can be capped and branded, at 650. The caps can be pre-branded, blank, or a combination of pre-branded and blank. For example, as illustrated in FIG. 6A, in some embodiments, all bottles can be capped with blank caps, at 651, and some or all of the bottles can be branded with caps which have various pre-printed branding information, at 652. In other embodiments, all bottles can be capped, at 653, with various pre-branded caps. In such embodiments, no further branding may be necessary. In still other embodiments, bottles can capped, at 654, with a mix of blank caps and pre-branded caps and some or all of the bottles capped with blank caps can be branded, at 655. When bottles are capped, at 650, the caps can be singulated, oriented, and applied with predictable torque to each bottle. In various embodiments, selection of cap branding, selection of caps, affixing of caps to contains, printing of labels, affixing labels to caps, printing on caps, and/or filling containers with product can occur or various orders.

In embodiments, for example, where at least some of the bottles are branded with blank caps, a carrier and/or bottle and/or container can be transported to a branding station that can brand caps, at 652 or 655, with cap labeling information (e.g., logos, graphics, artwork, text, etc.) that can be specific to each cap. A cap can be, for example, a cover, a lid, a top, a plug, a stopper, or any object used to partially or totally seal and/or close a container. A branding station can include, for example, a printing system that can print the desired labeling information on adhesive backed label web. A column of the labels can be transferred to a vacuum belt assembly that can, for example, change its lateral spacing and apply the labels to the bottles in the carrier. In various embodiments, various of the stations and/or actions can be combined and/or separated and the actions illustrated in FIG. 6 can be performed in various orders. For example, capping and branding can occur at different stations. Also, in some embodiments, the caps can be branded before being applied to the bottles, while in other embodiments, the caps can be branded after being applied to the bottles.

Some embodiments can include verifying that a branded cap is capped on the correct bottle by using, for example, a bar code, a vision system, and/or Radio Frequency Identification (RFID). In some embodiments, it is possible that a verification process will determine that an error has been found. When this occurs, it is of benefit to provide systems and methods that can remedy the situation. Some embodiments can fix the bottle by, for example, removing the incorrect cap and applying a new and corrected cap or label and/or by rescheduling a prescription. Some embodiments for correcting mistakes can be combined with systems and methods that, for example, apply caps and labels. Some embodiments can be either automated, manual, or various combinations of the two. For example, some embodiments may require additional inspection by medical personnel such as a pharmacist or by other trained personnel that are capable of inspecting the containers for correctly branded caps. In addition, in further alternative embodiments, instead of, or in addition to, the cap being branded, the container/bottle may alternatively be branded using the techniques and process described herein by either printing on the container and/or utilizing pre-branded containers. For example, various branding information can be applied around the top portion of a bottle and/or container and/or on the bottom of a bottle and/or container.

Figure 7:
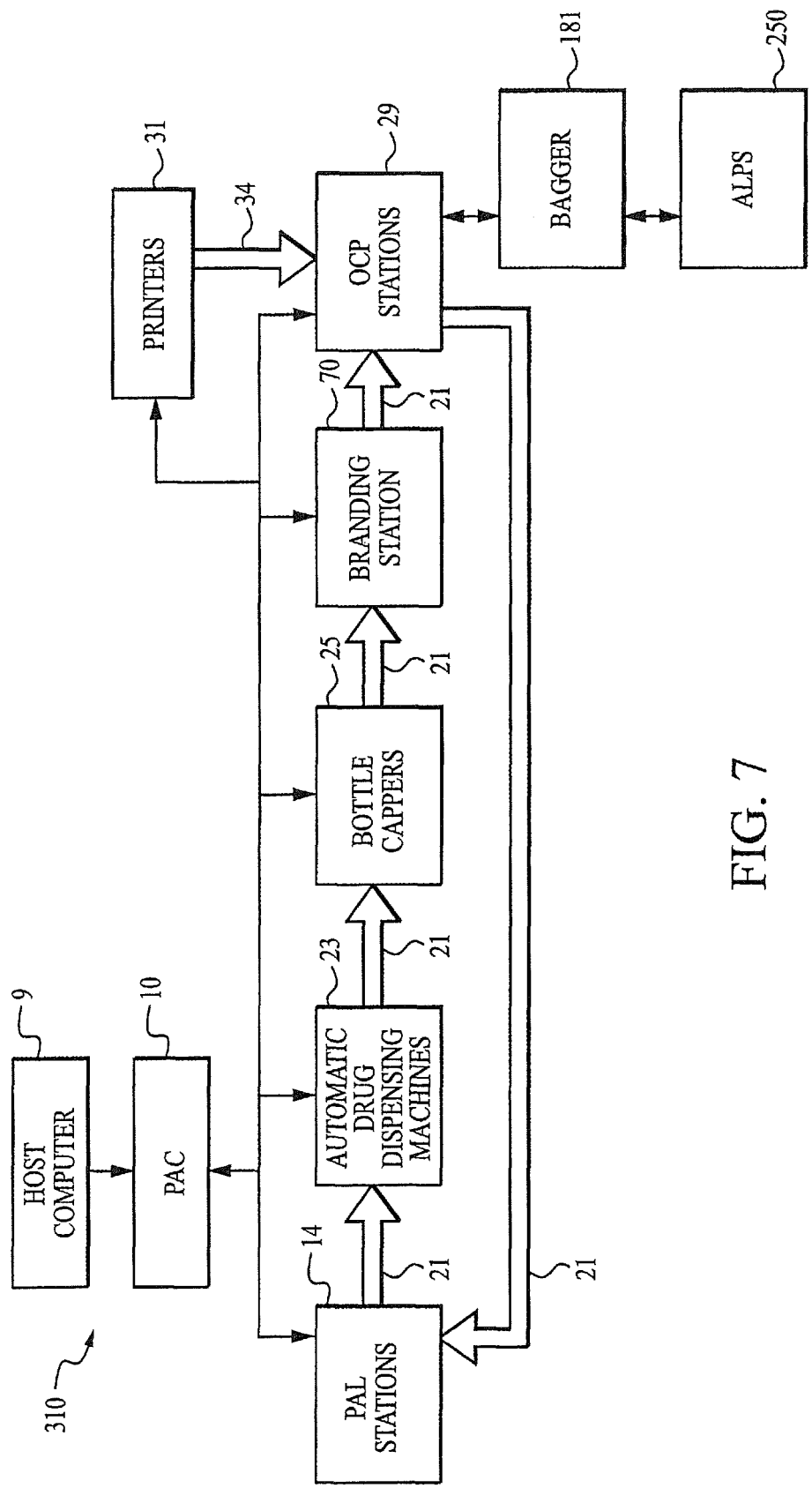
FIGS. 7-8 are diagrams illustrating automated pill dispensing systems in accordance with some embodiments of the disclosed subject matter
Figure 8:
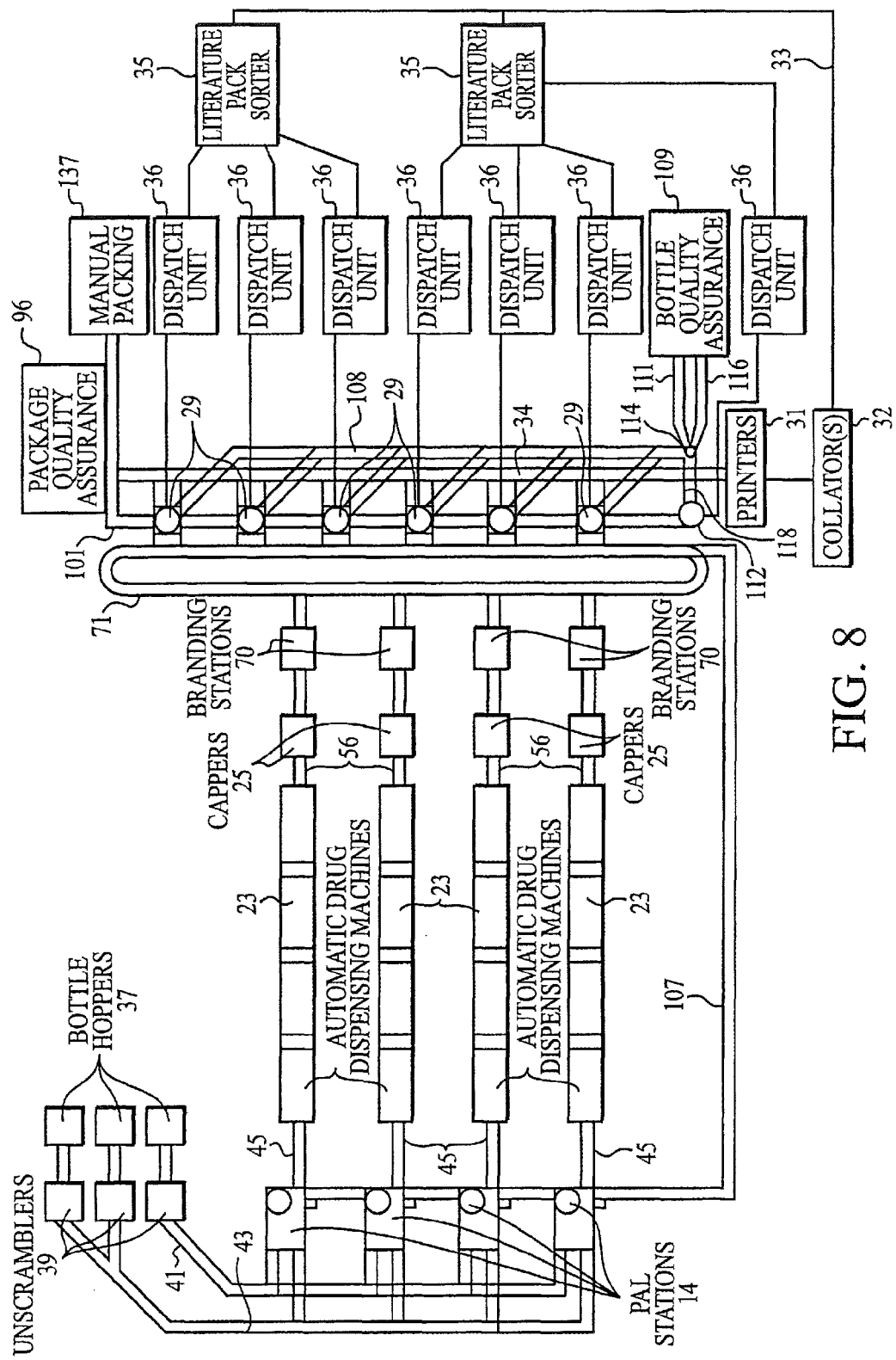

As illustrated in FIG. 7 and FIG. 8, in some embodiments, a branding system 70 can be located, for example, between bottle cappers 25 and OCP stations 29. In some embodiments, capping and/or branding, at 650 of FIG. 6, can be performed, for example, by bottle cappers 25 and branding system 70. For example, with reference to FIG. 6A, capping, 651, 653, and 654 can be performed by bottle capper 25 and branding, at 652 and 655 can be performed by branding system 70. In other embodiments, bottle cappers 25 and branding system 70 can be integrated as one system.

Figure 9:
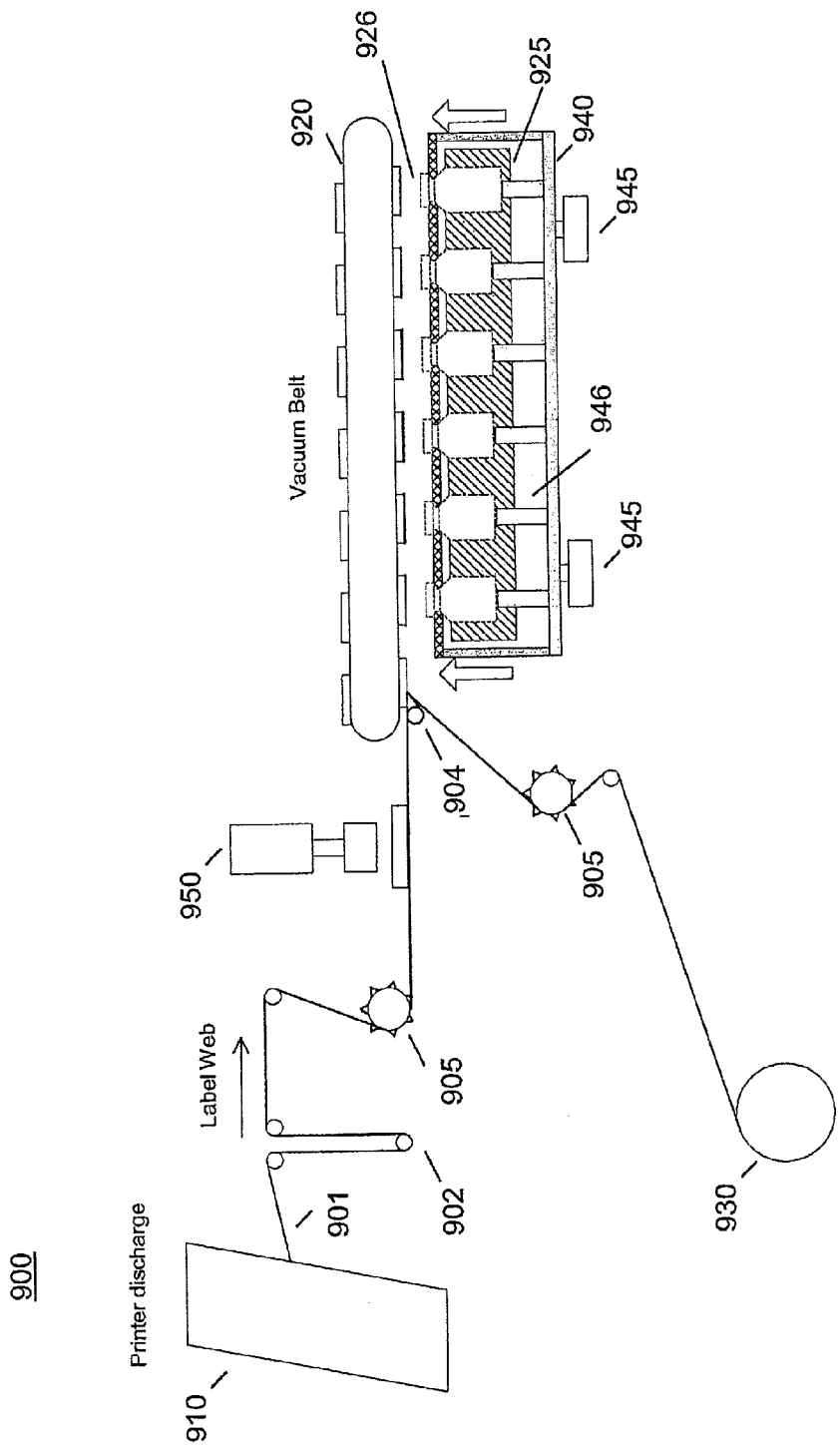
FIG. 9 illustrates a system that can be used for branding bottle caps in accordance with some embodiments of the disclosed subject matter.

FIG. 9 illustrates one embodiment 900 of a branding system 70 that can be used, for example, to print and apply labels for branding caps and/or the containers associated therewith. As indicated above, alternative embodiments include utilizing pre-printed branded caps and/or bottles, or printing on the caps/bottle during the dispensing process. Branding system 900 can process a label web 901 that includes die cut cap labels, which can be, for example, in a 4×6 pattern and can be fed into branding system 900 on continuous web 901 with tractor feed perforations. The web 901 can be driven by tractor feeders 905. Web 901 can be fed through a printer 910, through a take-up dancer assembly 902, and around a label peel bar assembly 904. Printer 910 may be a printer of various types, including for example, a laser printer, an inkjet printer, a thermal printer, a solid ink printer, etc. A row of labels can be peeled by peel bar 904 and a vacuum belt assembly 920 can position a receiving head to pick up the labels and transport them to position.

When the vacuum belt 920 is populated with labels, a bottle carrier 925 can be lifted so that the bottles 926 make contact with an adhesive side of the labels. The bottle carrier can be held in a carrier lift platform 940 and can be raised by lift cylinders 945 and/or lift pins 946. The pressure in a vacuum manifold can be reversed so that the labels positively released from the vacuum belt assembly 920. The carrier 925, now carrying branding and capped bottles, can be lowered and discharged onto a take away conveyor spur. The empty label web can be, for example, collected by a take-up reel 930.

Figure 10:
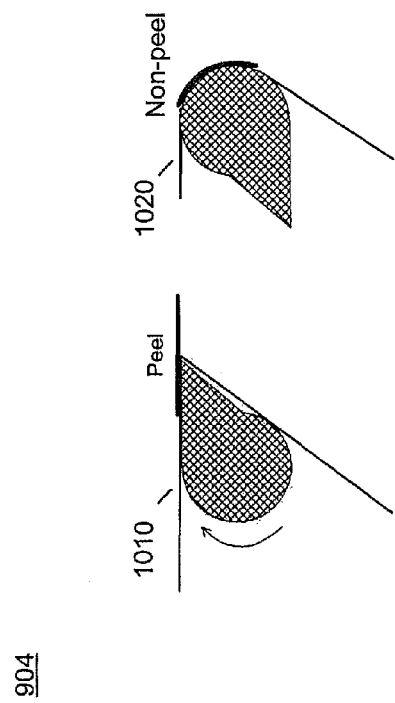
FIG. 10 illustrates a peel bar in peel and bypass positions in accordance with some embodiments of the disclosed subject matter.

In some embodiments, label positions can be removed before a web travels across the peel assembly 904. This can be achieved, for example, by a die punch 950 that can remove designated labels and web backing material. The die punch 950 can punch out the labels so that no label is affixed to various of the bottle caps and can be controlled on a per label or per row basis. In some embodiments, the peel operation can be aborted. For example, if the ID of a carrier does not match the bar code of the label array that is being transferred onto the vacuum belt assembly 920, the label peel assembly operation can be aborted. One way of accomplishing this is illustrated in FIG. 10. A peel assembly (e.g., 904 of FIG. 9) can be moved into, for example, a peel position 1010 or a bypass position 1020.

When a carrier of array labels has been aborted, some embodiments can recover. For example, additional label arrays can be removed until the correct label array for the current loader arrives. Another option is to re-print the correct labels for a carrier 925 that is currently loaded and possibly for carriers that are staged. The label web 901 can be advanced and bypassed until the correct label array arrives at the peel assembly 904.

Some embodiments can allow a carrier 925 to pass through a branding system without being branded. This may be done, for example, if a customer does not want some or all of the caps to be branded, but bottles are being processed by, for example, system 900. This can be done, for example, by putting the peel bar 904 in the bypass position, 1020 of FIG. 10, or by pausing the label web 901 while a carrier 925 is being processed. Alternatively, an entire carrier can be bypassed by having that carrier skip the branding station 900.

Various branding stations 900 can be operated independently. When a station 900 is available for work, it can generate a message indicating its availability to a carrier transport system. In addition, if an equipment or process alarm causes loss of operating capability, a station 900 can generate a message to a carrier transport system reporting this condition. When a branding station 900 is off-line, a different branding station 900 can receive the balance of the workload. For example, a transport system can divert bottle carriers 925 there.

Branding stations 900 can process carriers at various speeds. For example, in some embodiments a branding station can have a cycle time of 65 seconds or faster per carrier. In some embodiments, an ADS system can have a throughput of 7700 bottles per hour an in cases where every carrier is fully populated, this translates to 5.3 carrier per minute or one carrier every 61.3 seconds.

Figure 11:
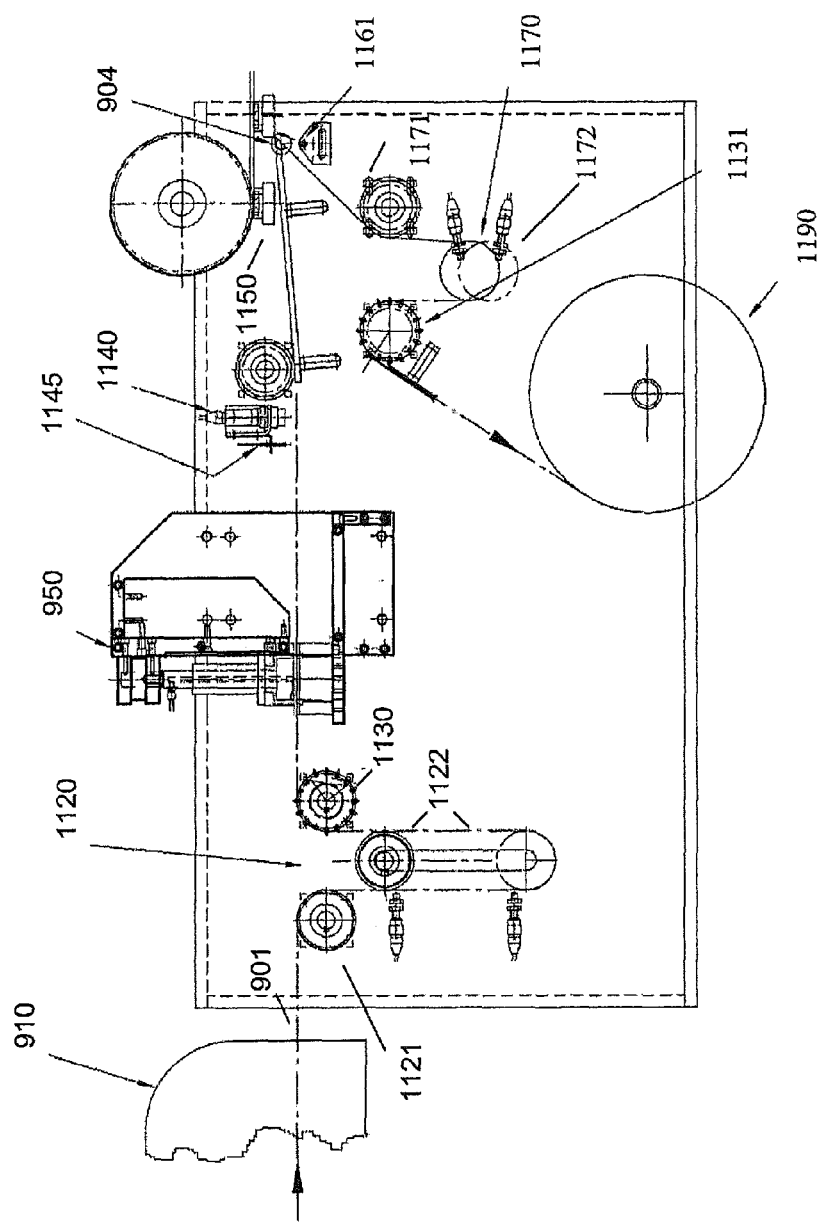
FIG. 11 illustrates a more detailed view of a system that can be used for branding bottle caps in accordance with some embodiments of the disclosed subject matter.

FIG. 11 illustrates a more detailed view of some embodiments a branding system 900. A label web 901 can be fed from a printer 910 to an in-feed accumulation system 1120. An entrance idler roller 1121 can be part of in-feed accumulation system 1120. A vertical moving dancer roll 1122 can provide accumulation of web stock between a printer 910 and an in-feed tractor drive roller 1130 to compensate for the possibly continuous in-feed from the printer 910 and intermittent out-feed created by label application to a vacuum assembly belt 904. A series of sensors can detect the dancer roll 1122 position and control the in-feed/out-feed equilibrium of the web 901. The dancer roll 1122 can use a counterbalance to minimize web tension and inertial applied to the web as a result of its movements. In-feed tractor roller 1130 can be driven in conjunction with a discharge tractor roller 1131 to control the web 901 movement during vacuum belt label pick-up.

A punch and die system 950 can have, for example, four punch and die positions aligned with four labels rows of labels on the web stock 901. The punch and die system 950, can punch out any or all of the positions. That is, in some embodiments, each punch can be operated independently of the others. A punch can completely remove the label from web and can have, for example, a blow-off system to clear punched label from the die area.

A punch can also or alternatively be used a vacuum system to remove the punched labels. The vacuum and/or blow-off system can have an independently regulated air pressure source or sources. Position sensors can be included with a punch to, for example, indicate the successful execution of a punching operation. Each punch and die set can also include an alignment provision to ease replacement with new sets. A punch label verification system 1140 can include, for example, a sensor for each of the punches and sense and verify the removal of each punching operation. This sensor can be, for example, a photo type sensor with cordsets.

In some embodiments, prior to a label peel operation, a sensor, such as, for example, a registration sensor 1145 and barcode reader, can be used to position the label web with respect to the vacuum belt pucks 1150 for the subsequent label application. For example, printed barcodes on the label web 901 (for each respective carrier) can be read to ensure the proper set of labels are applied to each carrier cap.

A peeling system, such as, for example an articulating peel bar 904 can strip labels from the web 901 and transfer them to a series of vacuum pucks 1150 attached to vacuum belt drives. The label web 901 can be moved in unison and in registration with the vacuum belt to provide a reliable transfer of label to a puck. As discussed, two surfaces on the peel bar 904 can provide a label strip function or a label bypass function. For example, a web passing over a sharp edged surface can strip the labels; alternately a web passing over a rounded surface can permit the label to remain adhered to the web substrate. A rotating movement can articulate the bar between the sharp edge and rounded edge. This movement can be provided by, for example, a pneumatic actuator with speed control and stroke adjustment.

In some embodiments, air jets 1161 directed beneath the label transfer position can assist label placement onto the vacuum pucks 1150. This can be accomplished using, for example, a blow tube and independently adjustable air pressure regulation can be provided.

Proper web tension over the peel bar 904 can be maintained with use of a pressure regulated dancer roller of a web tensioning system 1170. Roller 1171 can use, for example, linear motion or rotational motion. A friction free/low friction pneumatic actuator can be used to provide the load to the dancer 1172. An independently regulated precision regulator can provide air pressure for this function. Sensors can detect dancer 1172 movement and can identify either a broken or jammed web condition.

A driven discharge tractor roller 1131, which can be mechanically coupled to the in-feed tractor roller 1130, can provide positive web movement and position. The tractor roller 1131 can be driven by, for example, an appropriate Servo-Drive System. Used label web 901 can be re-wound on a spindle, which can use web tensioning control to maintain a uniform pressure between the rewind 1190 and the discharge tractor roller 1131. A sensing system can be used to determine when the rewind spindle at 1190 is full.

Figure 12:
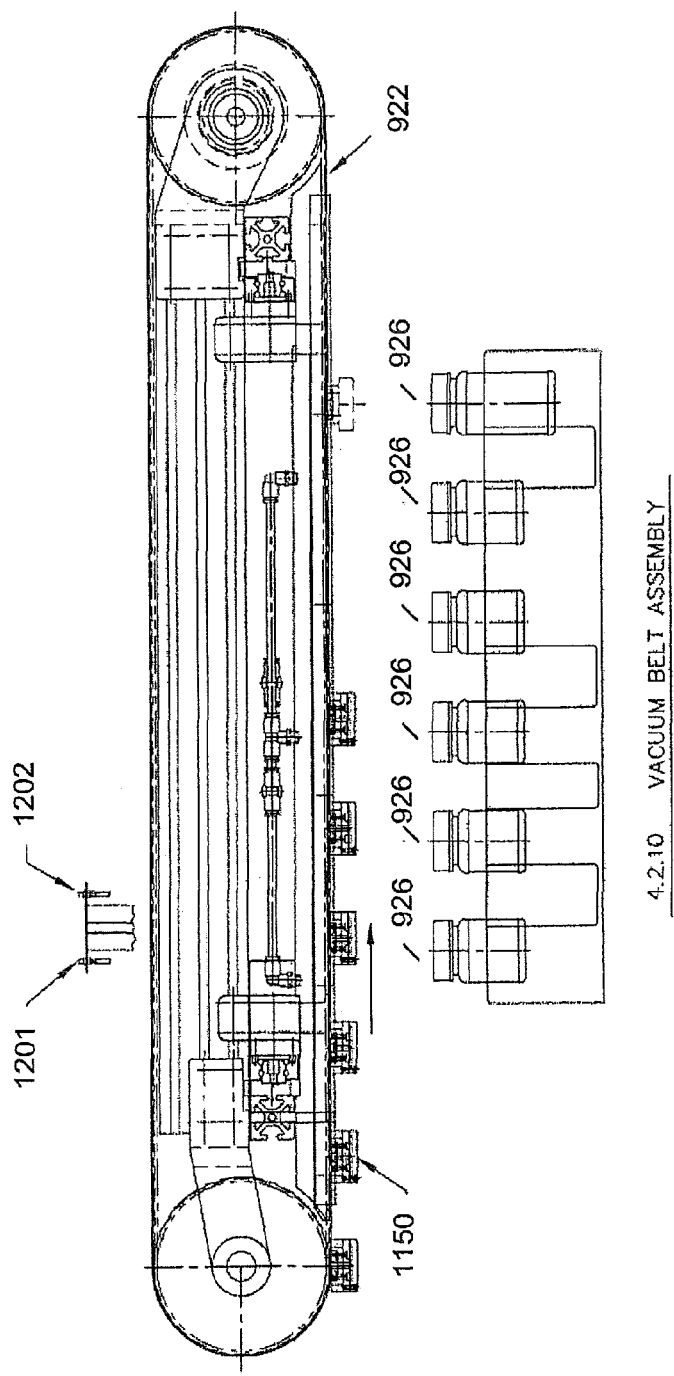
FIG. 12 illustrates a vacuum belt system that can be used in accordance with some embodiments of the disclosed subject matter.

An embodiment of a vacuum belt 920, is illustrated in FIG. 12. A number of these belts can be used in parallel. For example, for a carrier of 11 rows and six columns, four parallel vacuum belts with six vacuum pucks 1150 can be used to receive labels from the label web 901 and transport them for deposit on the container caps in a carrier 925. Each belt can carry a vacuum puck 1150 to deliver labels to each row of capped containers in a container carrier 925. The parallel vacuum belts 920 can move in unison, and can be mechanically connected to pass over the peel bar 904 where labels striped from the label web are applied to the vacuum pucks. After the labels are received, the belts can advance to a position over the containers for transfer to the caps.

In some embodiments, a belt 920 can move axially from a first position (inline with the web label spacing) to a second position (inline with the container spacing). Conveyor axial movement can be stopped with a fixed mechanical stop and axial movement can contain speed control and sensors to indicate successful actuation. Some or all of the parallel belts 920 can be driven, for example, by a common servo motor drive. A vacuum/pressure system can supply a vacuum belt 920 with vacuum pressure to hold labels to the vacuum pucks, then with positive pressure to deliver labels to the caps. Independent pressure and/or vacuum regulators can provide air pressure for these functions. The belt drive can be provided with sensors for a homing function and travel limit alarms, such as home sensor 1201 and travel limit sensor 1202.

Figure 13:
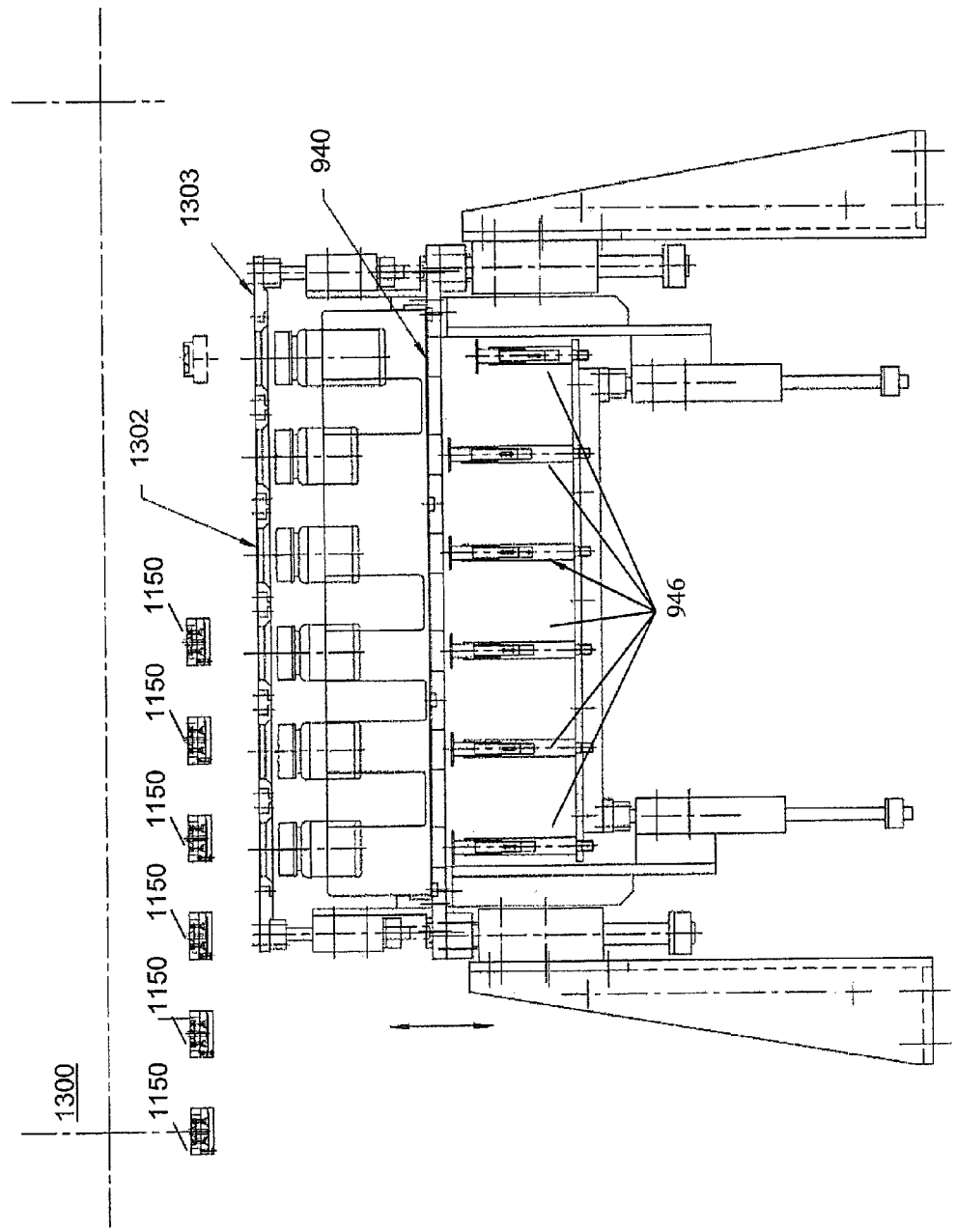
FIG. 13 illustrates a container/carrier handling station that can be used in accordance with some embodiments of the disclosed subject matter.

In some embodiments, carriers 925 can be transferred from a staging conveyor to a carrier entrance shelf. (e.g., 940 of FIG. 9). As illustrated in FIG. 13, a carrier 925 can be pushed onto a carrier lift platform 940, of the carrier handling station 1300. The carrier lift platform 940 can be located beneath the vacuum belt pucks 1150. In some embodiments, four operations can be executed to transfer the labels to the container caps. For example, a set of locators 1302 can engage a container carrier 925 securing its position. Container caps can be centered by the cap locating plate 1303 which aligns the caps with the labels being transported by the vacuum belt pucks. A carrier can be raised by the carrier lift platform 940 so that the container caps are positioned just below the vacuum belt pucks. Each container can be raised by individual push rods 946 until all containers caps come to rest against the adhesive side of the label carrying pucks, which can transfer the labels to the caps. Operation can then be reversed to prepare a carrier for exit from the carrier handling station 1300. The labeled container carrier can be pushed from the carrier lift platform 940 onto a discharge conveyor. Movements can be executed by speed regulated pneumatic actuators with, for example, stroke detection sensors to indicate successful actuation. The pneumatic actuators can have adjustable strokes as needed. Replaceable cap locating rings 1302 can be used on the cap centering plate. A carrier "in position" detector can be used to detect and indicate whether a carrier 925 is in the appropriate position in system 1300.

Figure 14:
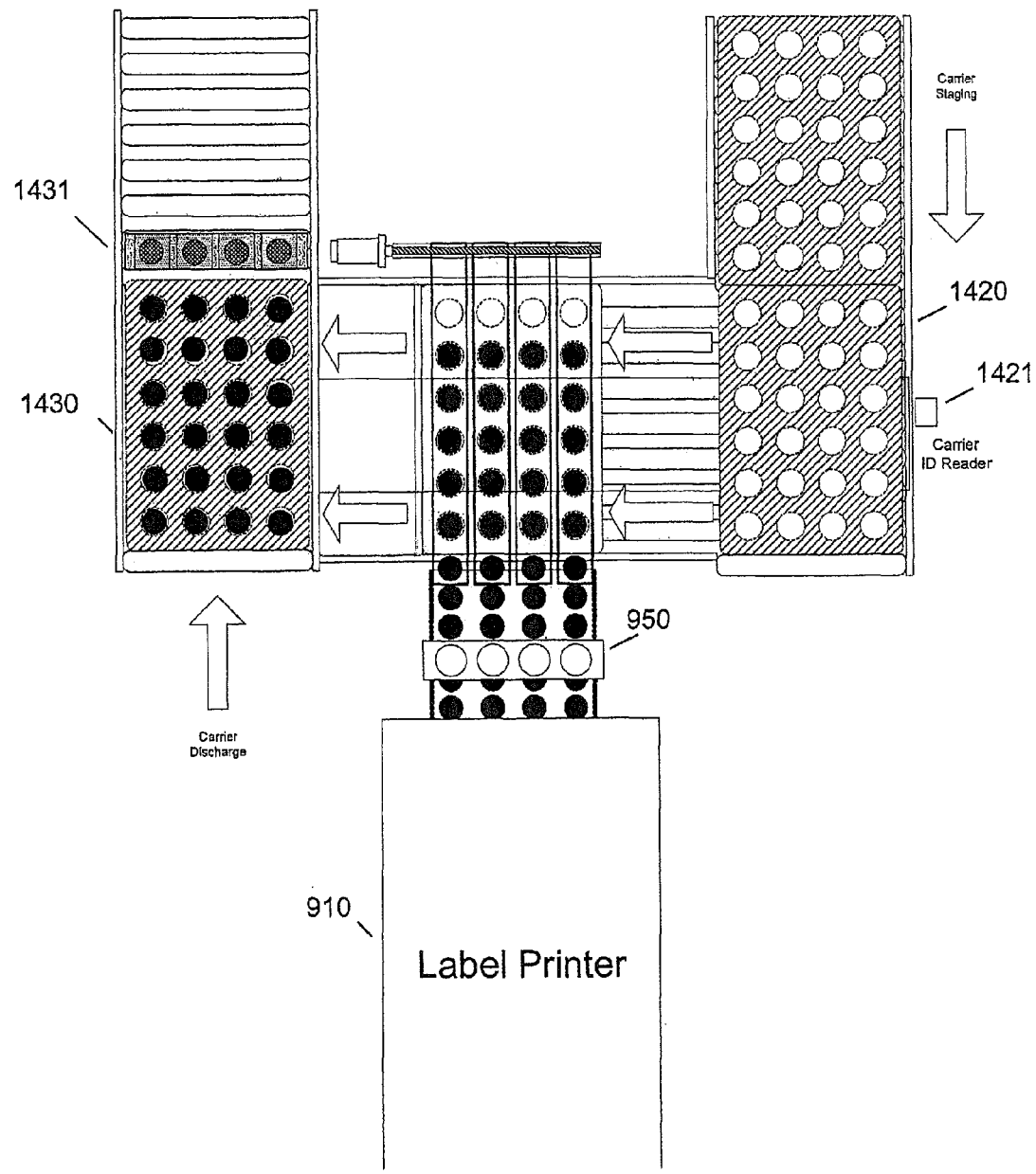
FIG. 14 illustrates an elevation layout of a portion of branding system that can be used in accordance with some embodiments of the disclosed subject matter.

FIG. 14 illustrates an elevation lay-out of some embodiments of embodiments of a branding system 70. For example, when a carrier 925 arrives at a branding station 900 it can be staged on an accumulation conveyor 1420. The carrier ID of a carrier 925 can be read by carrier ID reader 1421 so that a branding station 900 can be informed of which carrier is about to be processed. The carrier ID can correspond to a cap map that identifies each bottle by its position in the carrier. This information can be used so that a branding system 900 knows which bottle cap to brand with which branding information.

After being processed by a branding station 900, a carrier 925 can be discharged onto to a take away conveyor 1430. An inspection system 1431 can be included. Inspection system 1431 can included a four camera vision inspection system that can acquire an image at each row position. System 1431 can use pattern recognition to verify that the correct branding information has been applied to each bottle. A branding station 900 can generate a message to a carrier transport system that reports the carrier ID and reports whether each bottle position was correctly branded.

Figure 15:
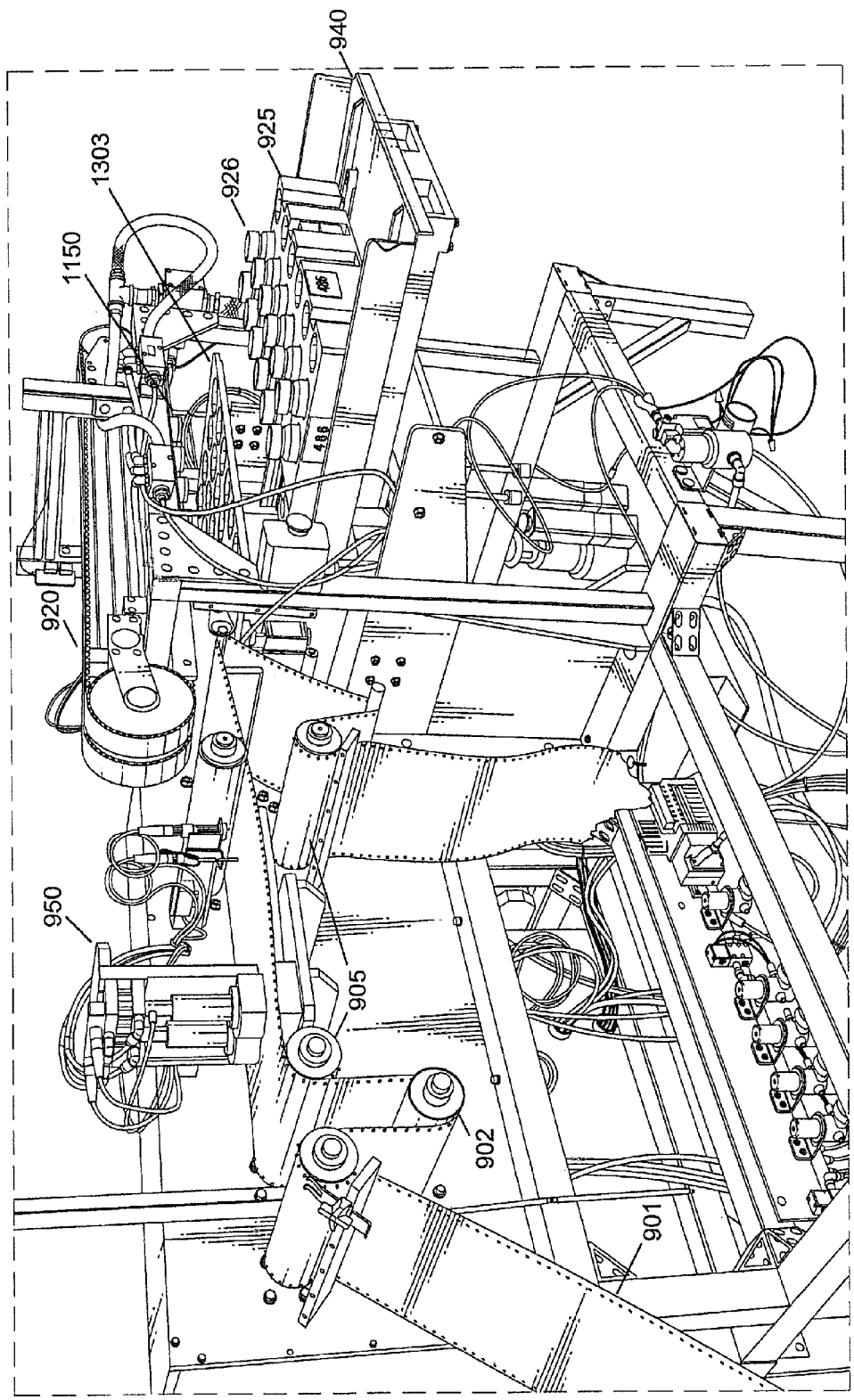
FIG. 15 illustrates a drawing of a photograph of a system that can be used for branding bottle caps in accordance with some embodiments of the disclosed subject matter.
Figure 16:
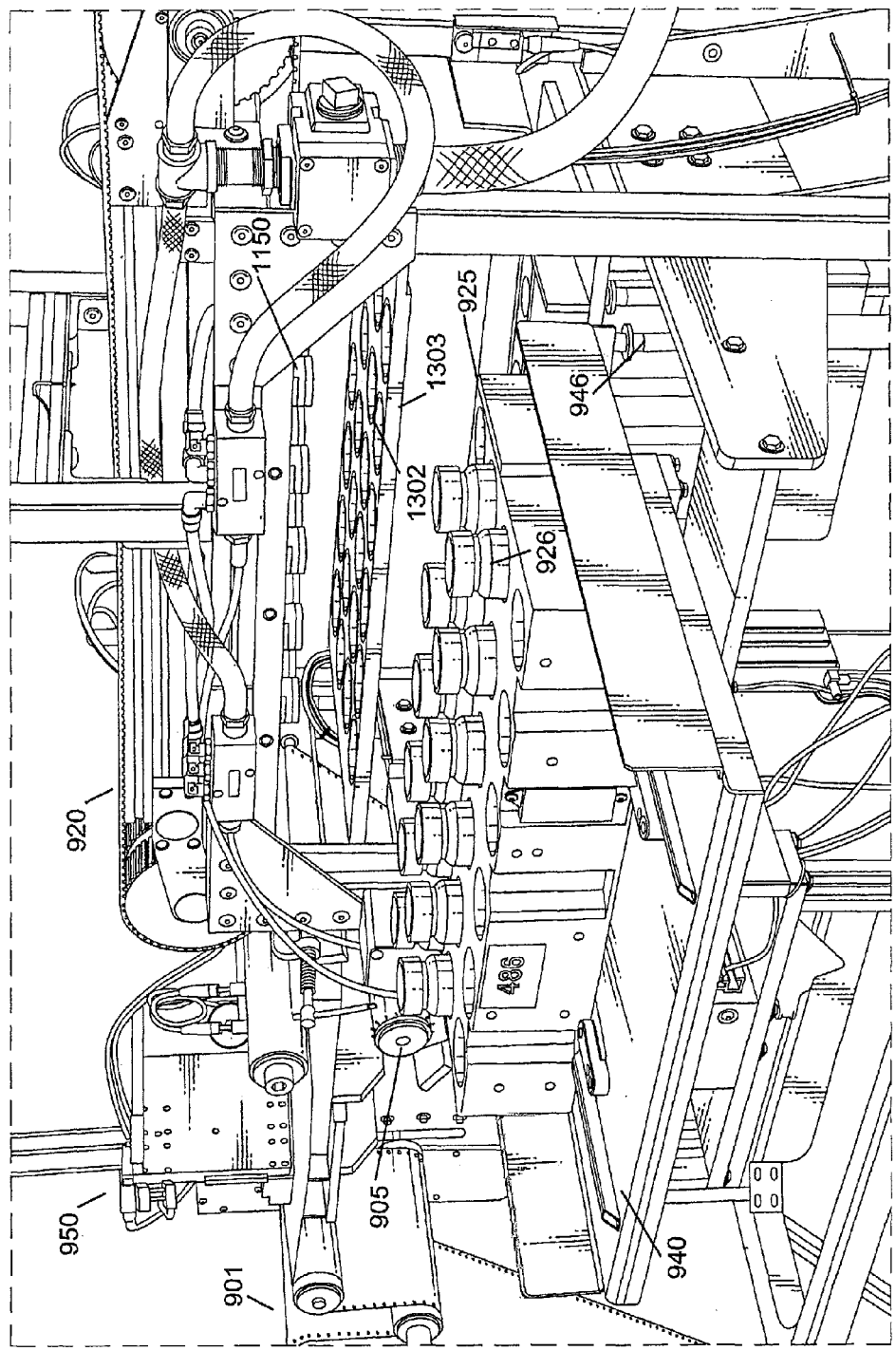
FIG. 16 illustrates a drawing of a photograph of a different view of the system illustrated in FIG. 8.

FIGS. 15 and 16 illustrate drawings of a photographs of two different views of an embodiment of the disclosed subject matter. Various embodiments of various components of a system 900 are shown in FIGS. 15 and 16. For example, an embodiment of a system 900 including embodiments of label web 901, take-up dancer assembly 902, tracker feeders 905, die punch 950, vacuum belt assembly 920, vacuum belt pucks 1150, locators 1302, cap locating pate 1303, carrier 925, bottles 926, and carrier lift platform 940 can been seen in FIG. 15.

FIG. 16 illustrates a different view of the system 900 illustrated in FIG. 15. In particular, the lifting pins 946 can be seen under the carrier lift platform 940. Also, it can be seen that the carrier 925 is only half filled, with sixty two of the ninety four possible bottle positions occupied by capped bottles. Accordingly, in some embodiments, die punch 950 can remove the labels that would be affixed to the missing bottles prior to the label web 901 reaching the peeling bar In addition, vacuum pucks 1150 can be seen more clearly.

Returning to 653 of FIG. 6A, in some embodiments, the caps may be pre-branded and thus, a branding system 900 is not required. In such embodiments, the systems and methods can direct a bottles and/or bottle carrier to an appropriate capper and/or cap application chuck. For example, a capper can contain either "Co-Branded" caps or PBM caps. A capper can transmit "Station Type" information (for example, either "Branded" or PBM depending on the type of cap that it dispenses) to a carrier transport system. The carrier transport system can use the "Station Type" information to transport a carrier to an available capper that can service the carrier's needs. For instance, if the first available capper dispenses "Branded" caps, and the carrier requires "Branded" caps, the carrier can be diverted into that capper. Likewise, if the first available capper dispenses PBM caps, and the carrier requires PMB caps, the carrier can be diverted into that Capper. If the first available Capper does not dispense the type of cap required for the carrier, that Capper cab be bypassed. The directing may be accomplished, for example, by using an endless conveyer loop. In some embodiments, the pre-printed caps/containers are stored together and the system using various standard detection means to determine the appropriate cap/bottle to be dispensed. In alternative embodiments, the pre-printed caps/containers are stored in separate bin/locations for dispensing. When a branded container is used, similar systems described here can be used to deliver the appropriate container/package at the time of dispensing the medication and/or pharmaceutical. For example, an appropriate container, of various branded containers, can be selected and loaded into a carrier at a PAL station 14 of FIG. 8. In such an embodiment, a carrier 925, can carry contains of various brandings. In other embodiments, variously branded containers can be selected and filed without the use of carriers.

After a carrier arrives at a capper, its bar code ID can be read and the carrier's ID can be utilized to attain the "Cap Profile" associated with the carrier directly from a computer, such as a Pharmacy Automation Controller (PAC). The Capper can use the "Cap Profile" information to ensure that the required bottles (and only the required bottles) are affixed with the type of cap that it dispenses. The bottle capping may be controlled by a computer, such as a PAC, which refers to a cap map to determine the appropriate cap type for each bottle. In this case, the computer may control a robot arm to select the correct cap type for each bottle to be capped in a carrier and then place the cap on the bottle.

In some embodiments, a branding system may print directly on caps/bottles. For example, a pad printing system can be used that has different pads for each of the different brands. It is possible, however, that one pad printing machine may have several of the same pad. This can be useful for increasing throughput. In such a system, the addition of new brands may require new pads to be engraved and the use of fast drying inks may be beneficial. Dynamic printing of various logos is also possible by using, for example, a printing system that can print directly on bottle caps.

Figure 17A:
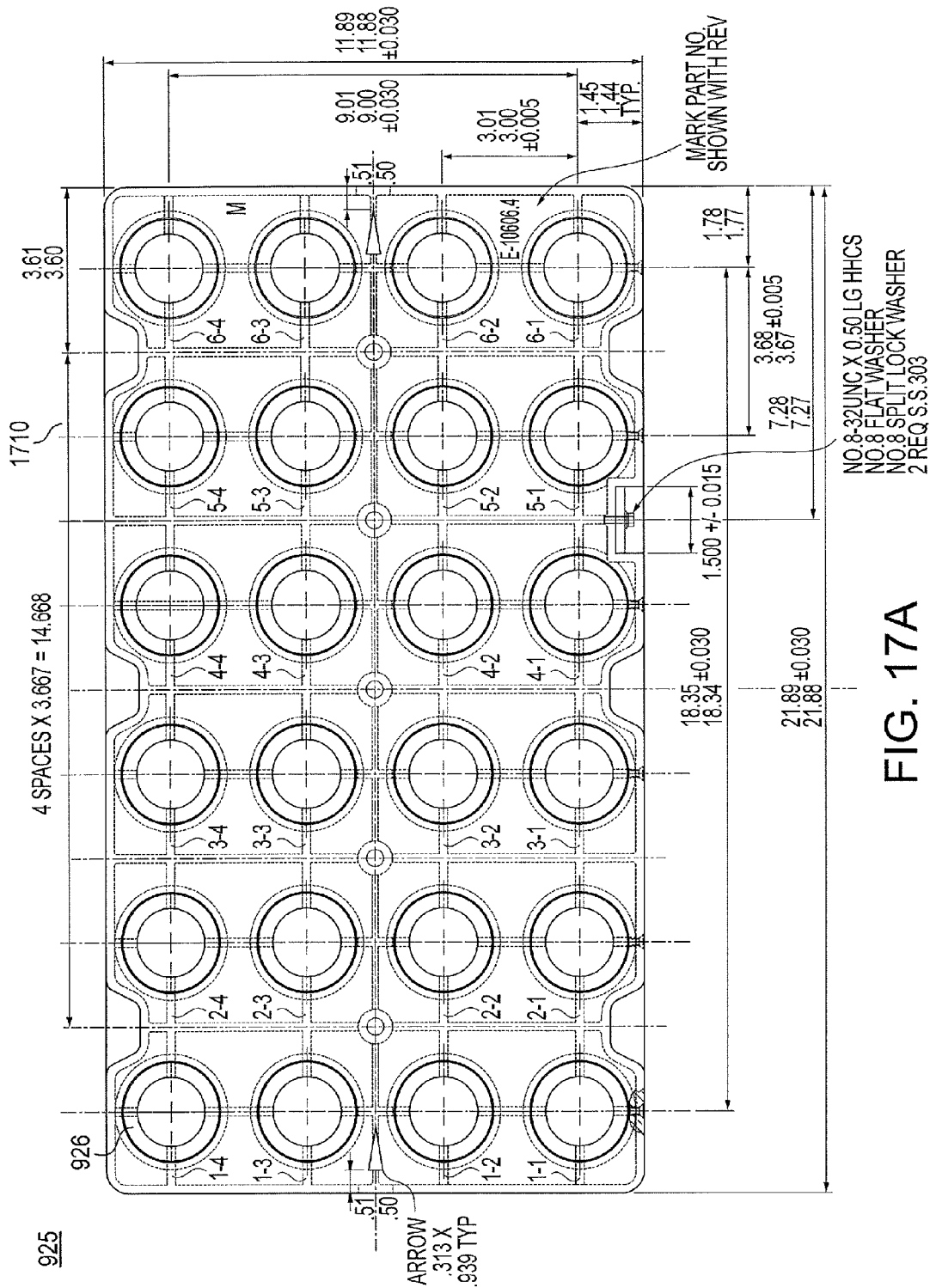
FIG. 17 illustrates three views of a bottle carrier that can be used in accordance with some embodiments of the disclosed subject matter.
Figure 17B:
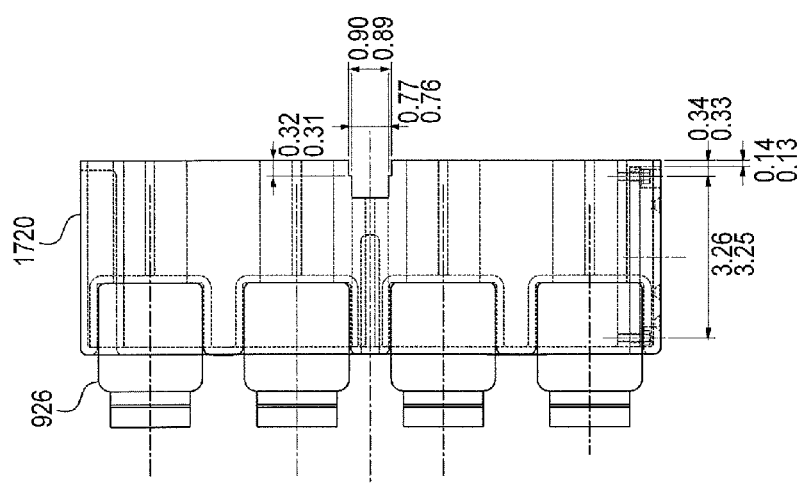
Figure 17C:
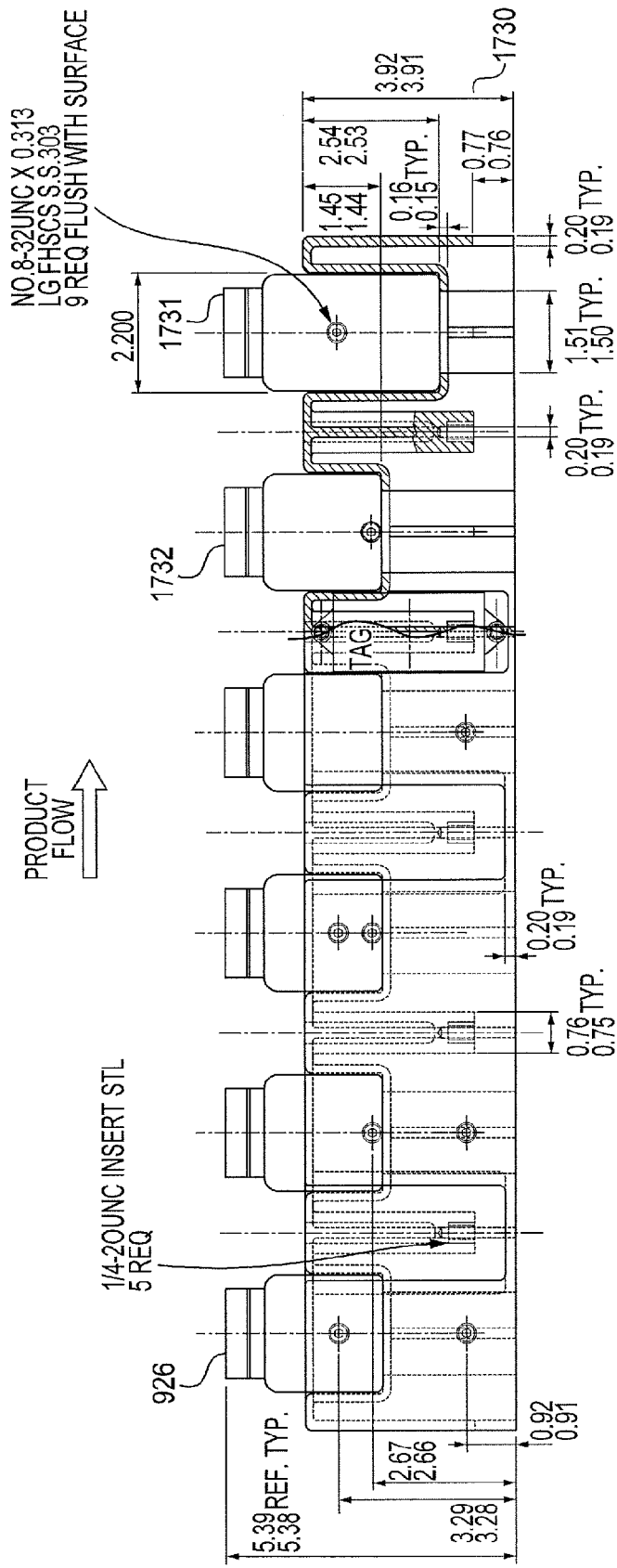

FIG. 17 illustrates an embodiment of bottle carrier 925 from a top view 1710, side view 1720 of four bottles in length, and side view 1730 of six bottles in length. As can be seen in view 1730, bottles of various heights can be accommodated in a single bottle carrier. For example, bottle 1731 is taller than bottle 1732. However, the tops of both bottles 1731 and 1732 have the same vertical position. The bottle carrier of FIG. 17 is only illustrative, various types of bottle carriers can be used.

Figure 18:
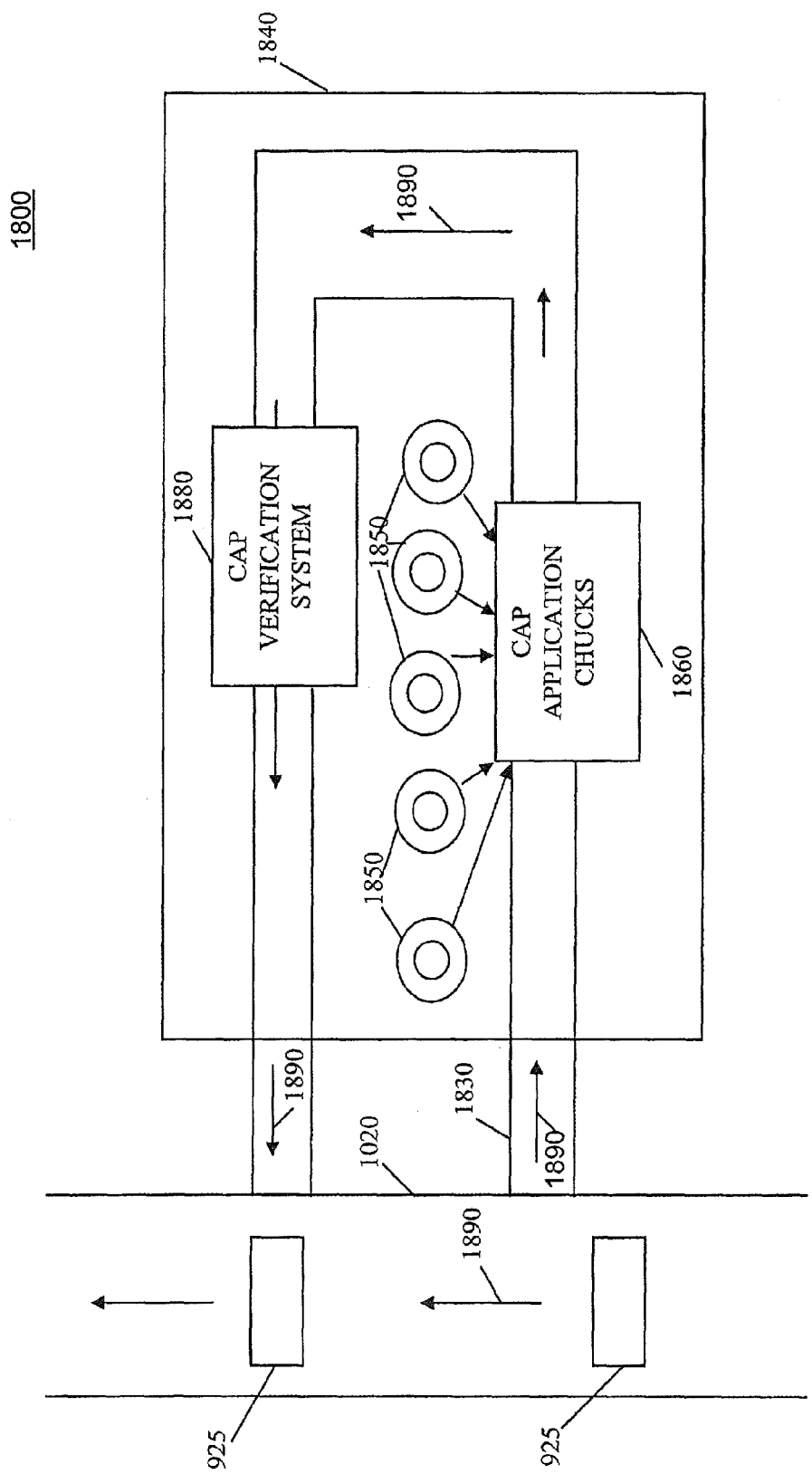
FIGS. 18-19 illustrates systems than can be used for capping and branding in accordance with some embodiments of the disclosed subject matter.
Figure 18A:
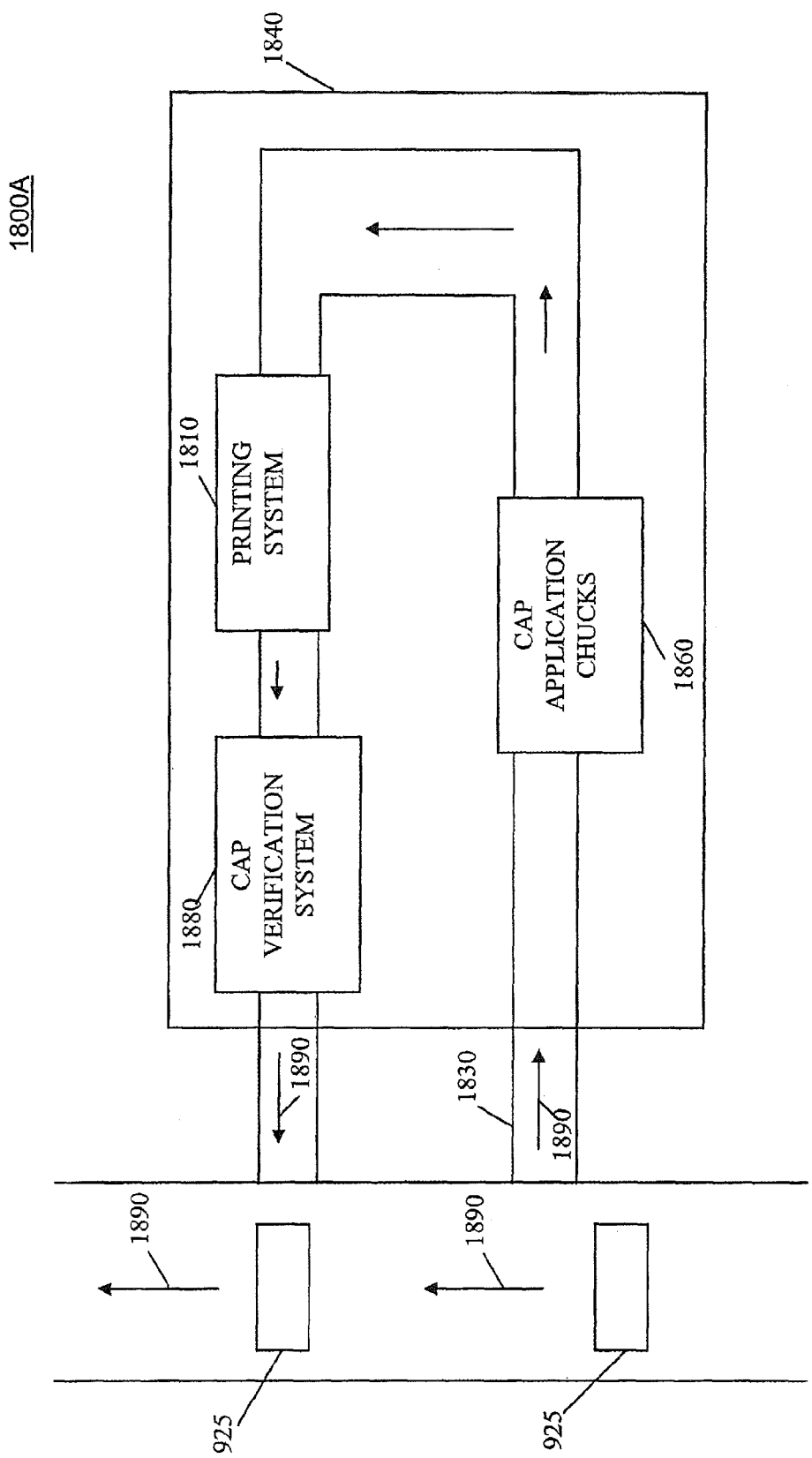

FIG. 18 illustrates an embodiment of an alternative and/or additional system 1800 for capping at, for example, 653 of FIG. 6A. A carrier 925 can travel on a carrier conveyor 1820 and be selectively directed to another conveyor 1830. Carrier flow is indicated by arrows 1890. Conveyor 1830 can bring a carrier 925 into a capping machine 1840 that includes a plurality of cap application chucks 1860 being fed by a plurality of vibratory bowl feeders 1850. Each of these vibratory bowl feeders can contain different cap types and the cap types may be fed to any one of the cap application chucks 1860. The type of cap fed to a chuck in 1860 can depend on the capping requirements of a bottle in a carrier 925 as defined by, for example, the cap profile. In other embodiments, system 1800 can include a printing system 1810, as illustrated in FIG. 18A as 1800A.

Returning to 654 of FIG. 6A, in embodiments where bottles are capped with a mix of branded caps and blank caps, at 654, a carrier can be processed by, for example, the system illustrated in FIG. 18 and/or by a branding system 900 illustrated in FIG. 9. This can be accomplished by capping some bottles with blank caps and some with branded caps by directing a bottle carrier to various cappers. Then, the bottle carrier can be directed to a branding system 900. The bottles that are capped with branded caps can be bypassed by, for example, moving the peel bar 904 to the bypass position for the appropriate labels or by punching out selected labels using a die punch 950. In some embodiments, conveyor 1820 can be part of or connected to, for example, conveyor 71 of FIG. 8.

Some embodiments of the disclosed subject matter provide various systems and methods for cap branding verification. For example, in some embodiments, after label application, a carrier 925 exiting the station can pass under a vision system, consisting of, for example, four independent cameras. The camera system can acquire the applied label images across each row of bottles. These images can be compared against a stored template and the matching image number returned to a control system. Embodiments can also return a no-match value for a label with, for example, a missing, incomplete, or miss-printed image. The control system can determine whether each bottle position image is correct and can pass the results of the inspection along to a Carrier Conveyor subsystem. The acquired image can be capable of being stored and retrieved for subsequent viewing and comparison against the stored templates. The number of stored images can vary, and in some embodiments, may be limited, for example, only by the size of a sub-system hard drive.

Various embodiments can compare information from the array of caps in carrier 925 to a cap map. In alternative embodiments, bottle carriers are not used and each bottle can be tracked based on alternative tracking methods, as opposed to a pre-designated location in a carrier. For example, bottles/packages/containers may optionally include means such as additional barcodes, etc. for matching the appropriate cap. These verification methods may confirm that the correct bottle contains the correct cap. If a mistake is found, that bottle may be sent for correction. Verification can take place at various location s. For example, referring to FIG. 8, verification can take place, for example, at branding system 200, between branding system 200 and OCP stations 29, at bottle quality assurance area 109, and/or at package quality assurance area 96. Referring to FIGS. 18 and 18A, verification can take place, for example, in the cap verification system 1880. In other embodiments, such as those where system 1800 is integrated with system 310 of FIG. 7, verification can take place in system 710 and/or system 1800.

Figure 19:
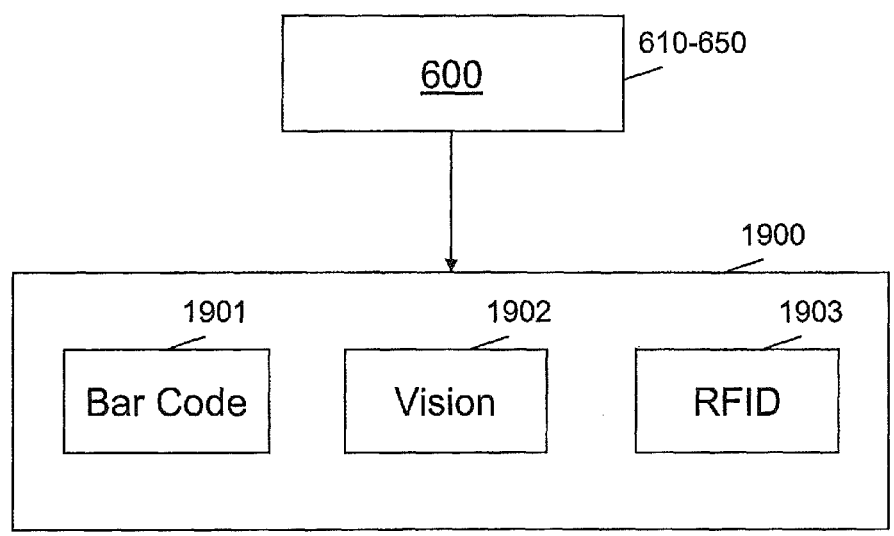

As illustrated in FIG. 19, verification can be performed after method 600 of FIGS. 6 and 6A and can use various methods, such as, for example, bar codes, vision systems, and/or RFID. In some embodiments using bar code verification 1901, a bar code, which indicates the brand requirements, is on the cap. The bar code may be, for example, maxi-code high density to limit the space requirements. The scanners can be downstream of the cap application and labelers, prior to the OCP's 29 and carrier rank buffers. The carrier ID is read. The cap map information can be downloaded from PAC to a local controller and/or computer to determine the required cap information. As the carrier passes under the scanners, the bar code can be read and verified. If an ID is not properly read, the bottle is flagged for inspection, for example, by manual inspection. The barcode may be any known in the art, including, for example, a standard 2D bar code.

In some embodiments, vision verification 1902 can be performed. This option is similar to bar code verification 1901, however a vision system is used to verify the cap branding. In this case, a controller and/or computer can be used for data collection and verification. An image of the entire array may be taken and compared to the cap map. The system may need to, for example, rotate the image from 0 to 360 degrees since the caps can be in any position.

In some embodiments, RFID verification 1903 can be performed. This option has an RFID readable tag as part of the label. This tag is unique to the brand. Carriers may be handled in the same way as options 1901 or 1902. An antenna can pick up the readable signal and determine if the proper brand is on the cap. In this option, there are several approaches that may be taken, for example, tagging of just the third party brand and none for the pharmacies, or tagging of all brands. Additionally, a logo may be printed on the RFID label.

As described above, when verification, using, for example, the above-disclosed systems and methods are performed on a bottle carrier and/or a bottle, it is possible that the verification process will determine that an error has been found with at least one bottle in the carrier. For example, a bottle can fail the verification process if the information on the cap is the not the information that corresponds to the bottle. When a mistake is found, it is of benefit to provide systems and methods that can remedy the situation. Such systems and methods can be integrated with the above-disclosed subject matter. However, that these additional embodiments of the disclosed subject matter need not be part of the systems and methods described above and in FIGS. 1 through 19. Instead the disclosed systems and methods can be used alone or in combination with any suitable systems and methods. Additionally, it should be noted that in alternative embodiments of the disclosed subject matter, manual intervention and/or manual processes can be substituted for one or more of the disclosed components. Accordingly, the disclosed systems and methods can be either automated, manual, or various combinations of the two.

Also as described above, bottle quality assurance area 109, of FIG. 8, can have several stations at which a pharmacist can, for example, scan the bar code on bottles and visually inspect the contents of bottles. The scan of the bottle bar code can bring up a display on the pharmacist's terminal which can includes all the information regarding the particular prescription and order. Such information can include, for example, the drug name, and instructions which identify the reason for the verification. Bottles that pass this inspection can be inserted or reinserted by the pharmacist on a bottle stream conveyer 111 to send the inspected bottles to the BSP station 112. Conveyer 108 can lead to a star wheel or other diverter mechanism 114 which, optionally under the control of a controller for BSP station 112, can deposit the bottle in a bottle stream conveyer 116 leading to the bottle quality assurance area 109 or into a bottle stream conveyer 118 leading to BSP station 112. Additionally, for example, at a quality assurance area 109 or other appropriate area, single bottles can be hand filled and capped by, for example, a pharmacist. These bottles can, for example, be scanned to identify order and/or branding information, put on a conveyor to a print station for cap decoration, and sent to a BSP station 112 to be, for example, bagged.

In some embodiments, when the order is a marriage order requiring some of the order to be manually filled and some of the order to be automatically filled, a portion of the order to be automatically filled can be filled by, referring to FIG. 8, the Automatic Dispensing Machines 23 capped by the bottle cappers 25, optionally in accordance with the Third Party Dispensing and branding described herein, and inserted into a bag or shipping container at an OCP station 29 along with the literature of the order. A bag can be diverted into a waiting tote 99, of FIG. 9 and sent on the conveyer 101, of FIG. 8, to manual packing area 137 where the rest of the marriage order requiring manual dispensing and packing can be packed with an automatically dispensed portion of the order, if appropriate.

Figure 20:
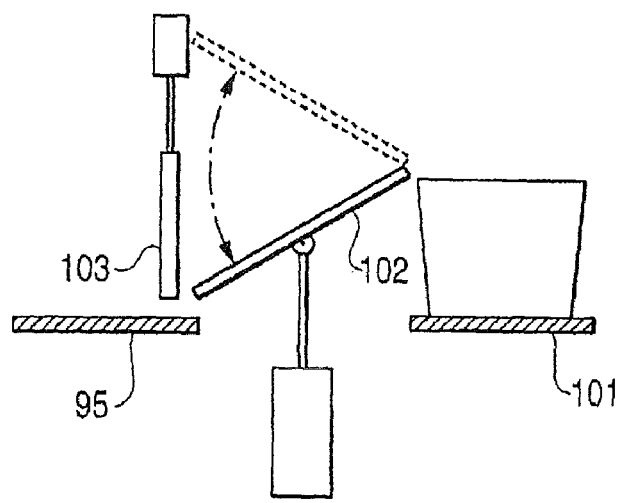
FIG. 20 is a perspective view of an OCP station that can be used in accordance with some embodiments of the disclosed subject matter.
Figure 21:
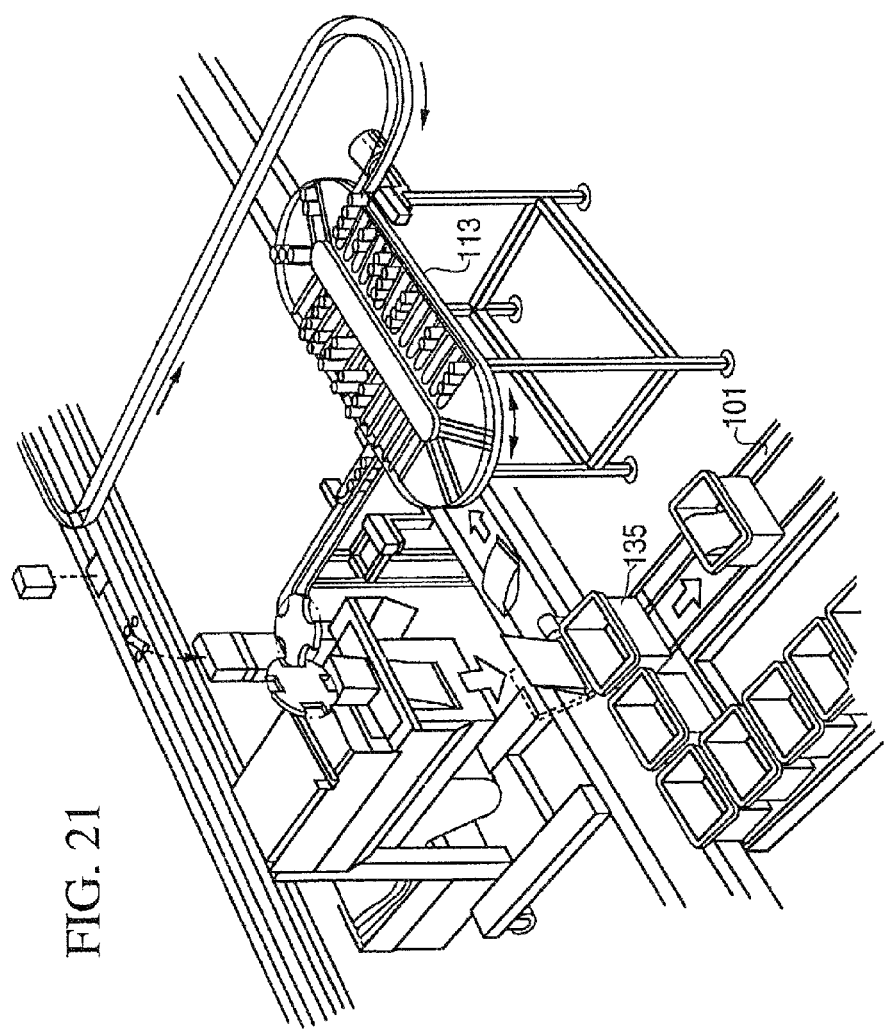
FIG. 21 illustrates a subsystem of an OCP station in accordance with some embodiments of the disclosed subject matter.

Additionally, as shown in FIG. 20, a bag can be dropped from the loading position onto an inclined table 102 and can slide under a gate 103 onto conveyor 95. If a bag is to be sent to the package quality assurance station 96, the gate 103 will be down to prevent the bag from sliding onto conveyor 95 and the table 102 is pivoted to dump the bag into a waiting tote on conveyor 101. As shown in FIG. 21 if a bar code reader detects, for example, that an envelope does not correspond to an order in buffer 113, then this envelope can be packed without bottles and the bag can be diverted into a tote 135 which can be carried by the conveyer 101 to the package quality assurance area 96 where the package can be manually assembled with the correct prescription bottles. The same or similar systems and methods can be used and/or adapted to send various packages and/or bottles to a quality assurance area 109.

In other embodiments, for example, when an order is a large production order requiring, for example, more than four bottles for the order, all items of the large production order can be found, in some embodiments, in the same rank of carriers and loaded onto a turntable at an OCP station. In alternative embodiments, bottles can be in different carriers and/or carriers are not used. In some embodiments, four bottles of the order can automatically be inserted into a shipping container along with the literature for the order and then this order upon being bagged can be diverted into a waiting tote which will remain at the OCP station to receive the rest of the order. The remaining bottles of the order can then be packed in an additional bag or bags and also diverted into a tote so that all the bags corresponding to a single large order can be assembled in a tote. When the order is complete in the waiting tote, the tote can be sent on the conveyer 101 to the manual packaging area 137 where the order can receive any manually dispensed prescriptions and can be packed manually into a mailing package for sending to the patient.

One embodiment of combining manual and automated systems and methods according to the disclosed subject matter can be, for example, capping, printing, and verification. In some embodiments, a pharmacist at, for example, at bottle quality assurance area 109, can fill a bottle with a prescription and insert the bottle, which is possibly in a carrier, in a printing system such as 1810 or branding system 200. The bottle or carrier can be inserted, by a pharmacist, into a cap verification system, such as 1880, to be verified. After performing appropriate methods, the bottle and/or carrier can be inserted or reinserted by the pharmacist on a bottle stream conveyer 111 to send the inspected bottles to a BSP station 112.

Figure 22:
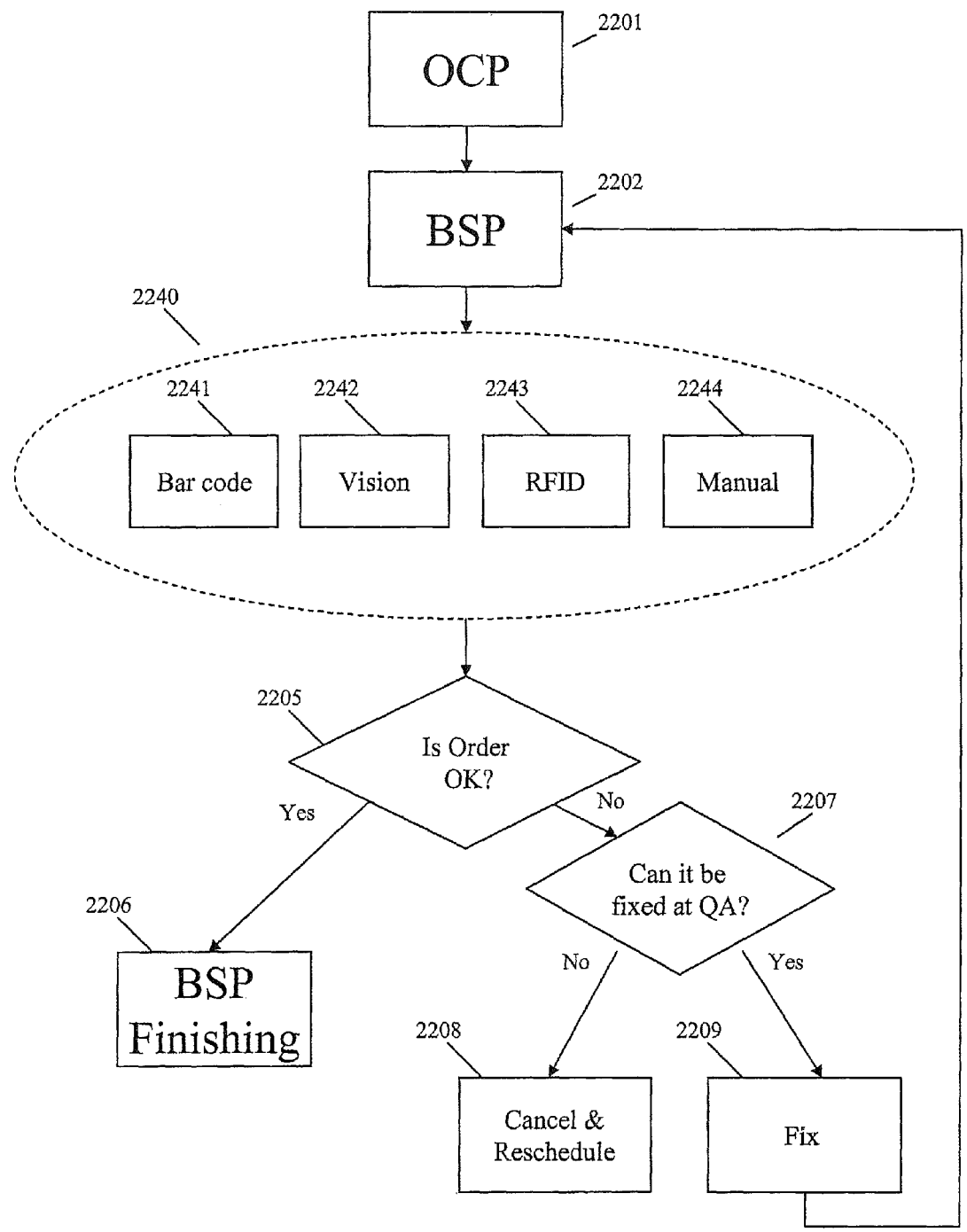
FIGS. 22-23 illustrate methods for branding, verification, and/or quality assurance in accordance with some embodiments of the disclosed subject matter.

One quality assurance alternative, which can be performed, for example, at bottle quality assurance area 109 is illustrated in FIG. 22. Accordingly, some embodiments of the disclosed subject matter can include, for example, branding system 900, cap verification systems 1880, printing systems 1810, dispensing machines 23, bottle cappers 25, and/or cap application chunks 1860 at quality assurance area 109. Product can arrive, at 2201, from an OCP station 29, and travel through, at 2202, a BSP station 112. It should be noted that the product can be a bottle itself or some number of bottles in a carrier. Additionally, verification can be, for example, performed at a bottle level or a carrier level. Product coming to this location may already have a cap applied and go through verification, at 2240, using for example, bar code 2241, vision 2242, RFID 2243, or manual 2244. It may be required to remove the cap to check the product inside the bottle, in this case, for example, manual 2244 can be used. If the cap is removed, that same cap can be applied after verification. If it is determined that the bottle has no problems, at 2205, it can be routed to a BSP station, at 2206.

If it has been determined, for example, that the incorrect cap was put on the bottle, at 2205, it can be determined if the bottle can be fixed at a quality assurance area 109, at 2207. Canceling and rescheduling the bottle, at 2208, can be performed if the bottle cannot be fixed at area 109. If so, the bottle and the prescription can be discarded and/or sent for restocking and the prescription can be rescheduled for filling. For example, a new bottle can be dispatched out of the bottle hoppers 37 of FIG. 8 and the process can be started again. If the mistake can be corrected at quality assurance area 109, then the bottle can be corrected, at 2209. Accordingly, a pharmacist can use embodiments of for example, branding system 200, printing system 1810 and/or cap application 1860, at 2209. It should be noted that, 2209 can include, for example, the application of branded caps, the application of pre-printed third party caps, and/or the printing and application of on demand caps. Upon correction, the bottle can be sent back to a BSP scanner, at 2202, and onto verification 2240.

In some embodiments, vertical bottle filling and bottle pre-pack can be inter-connected into the above described systems and methods. This can increase the level of automation, use less packaging, and increase the quality of cap branding. Vertical bottle filling and bottle pre pack can be integrated at a BSP scanner 112.

Figure 23:
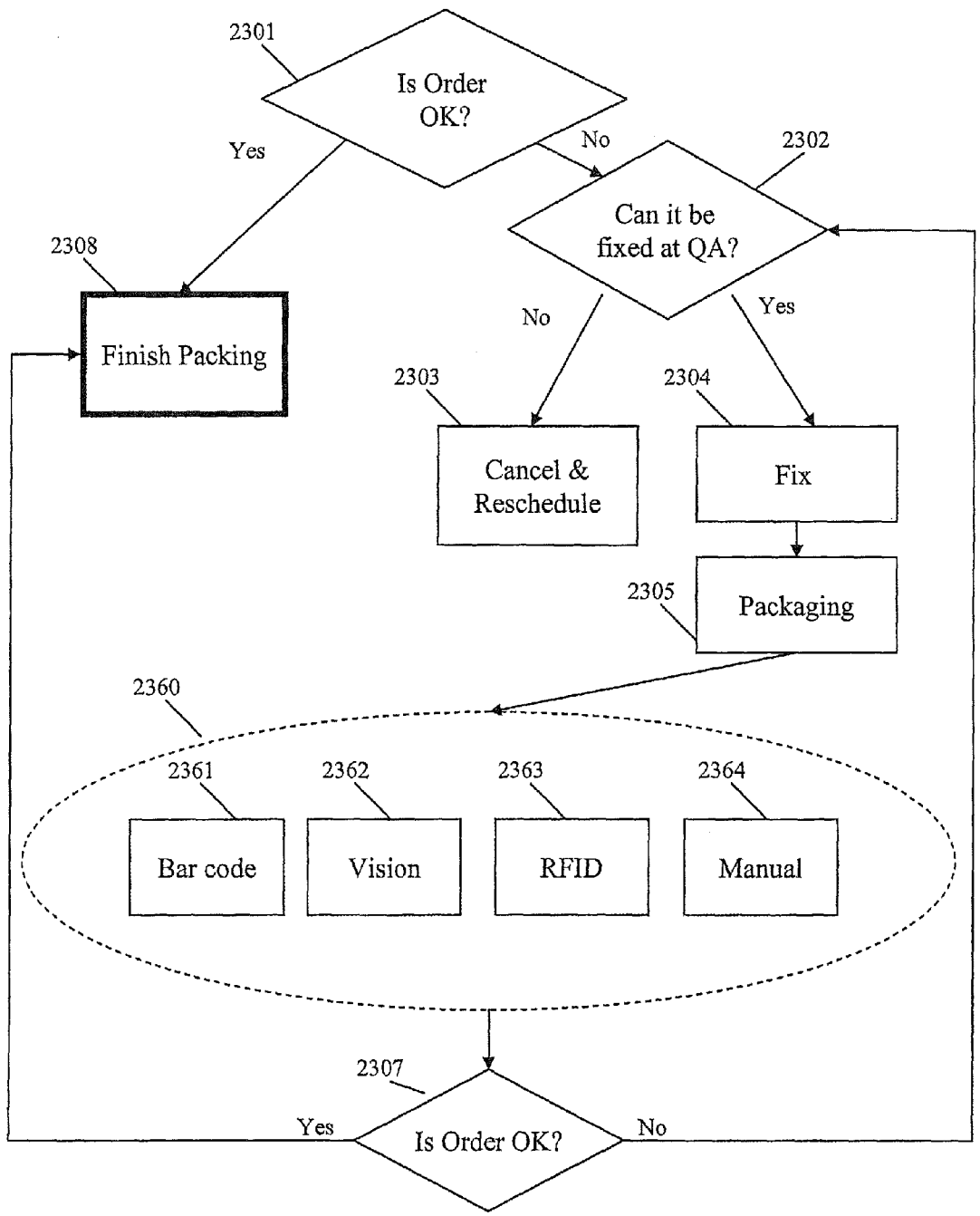

Another quality assurance alterative, which can be performed, for example, at bottle quality assurance area 109 is illustrated in FIG. 23. In this alternative if an order is checked, at 2301, and a problem is found, the order can be considered for fixing at quality assurance area 109. It can be determined, at 2302, if area 109 is able to perform the necessary functions and has the necessary supplies. If the order cannot be fixed, it can be canceled and rescheduled, at 2303, as described above. If the order can be fixed, it can proceed to be fixed and packaged at 2304 and 2305. It should be noted that, 2304 can be combined with or include, for example, the application of branded caps, the application of pre-printed third party caps, and/or the printing and application of on demand caps. Packaging, at 2305, can include any type of appropriate packaging. At, 2360, the bottle can be verified using any appropriate method, including the disclosed methods of, for example, bar code reading 2361, vision checking 2362, RFID checking 2363, and manual checking 2364. If the bottle, for example, is correctly capped, it can be sent, at 2307, to have any appropriate packaging completed at 2308. This may involve routing the bottle to a BSP station 112 to be sent on, for example, to a literature pack sorter 35. If the bottle and/or carrier is still not correctly filled and labeled, it can reenter the process at 2302.

Figure 24:
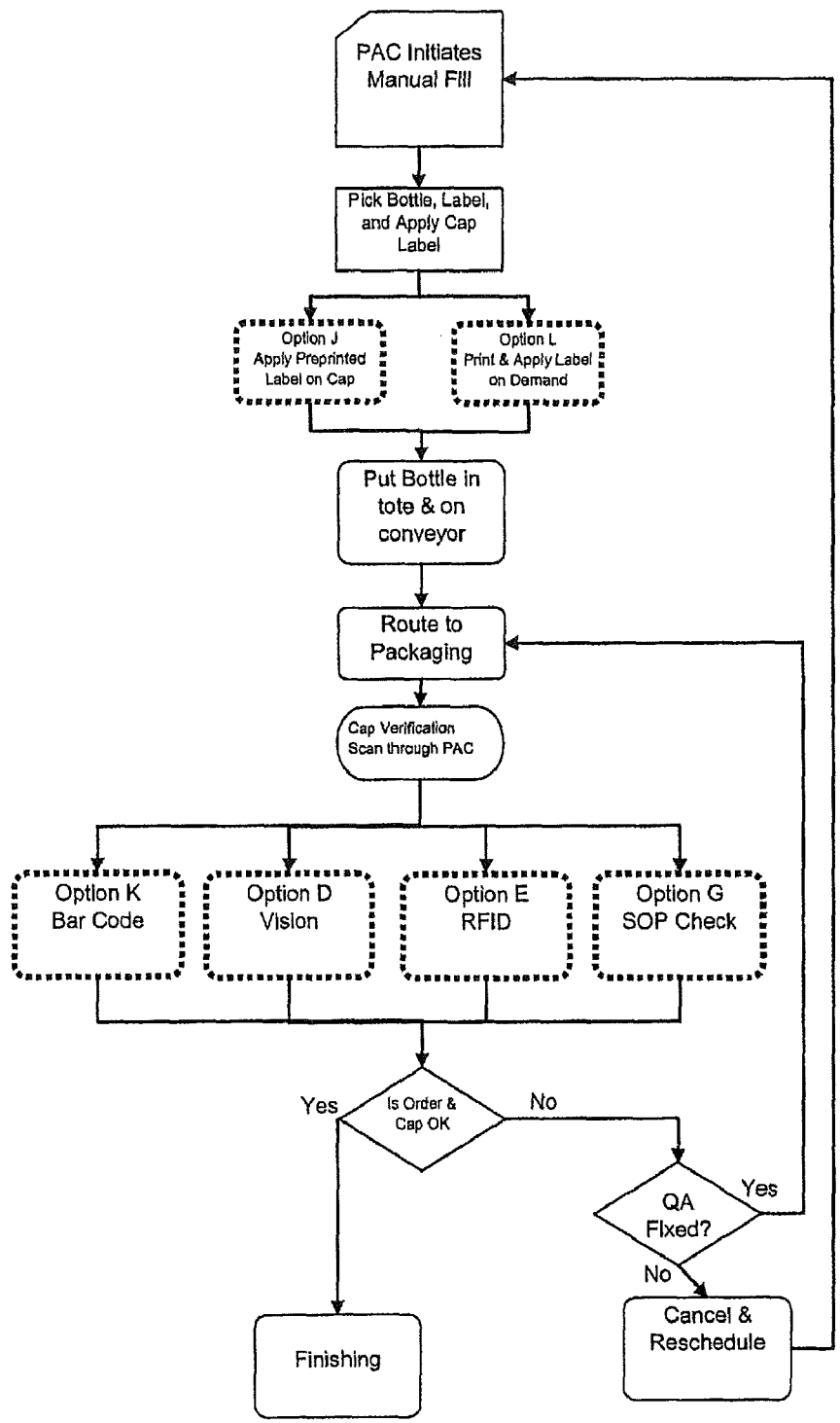
FIGS. 24-30 illustrate various alternative methods for branding, verification, and/or quality assurance in accordance with some embodiments of the disclosed subject matter.

Additional information regarding large volume dispensing, in accordance with some embodiments, is illustrated in FIG. 24. For example, if the product needs to have a branded cap, it may be applied downstream with a label. This can be performed either manually or automatically. Automatically may require additional capital for a typically low Rx count. Typically these are larger bottles—250-500 cc range. One option is to use a pharmacy (e.g., Medco) branded caps and then over-label with a branded label if required. In the finish package function, it is possible to require a cap scan for verification. In other embodiments, large volume product may be handled in any of the methods described above or below.

Figure 25:
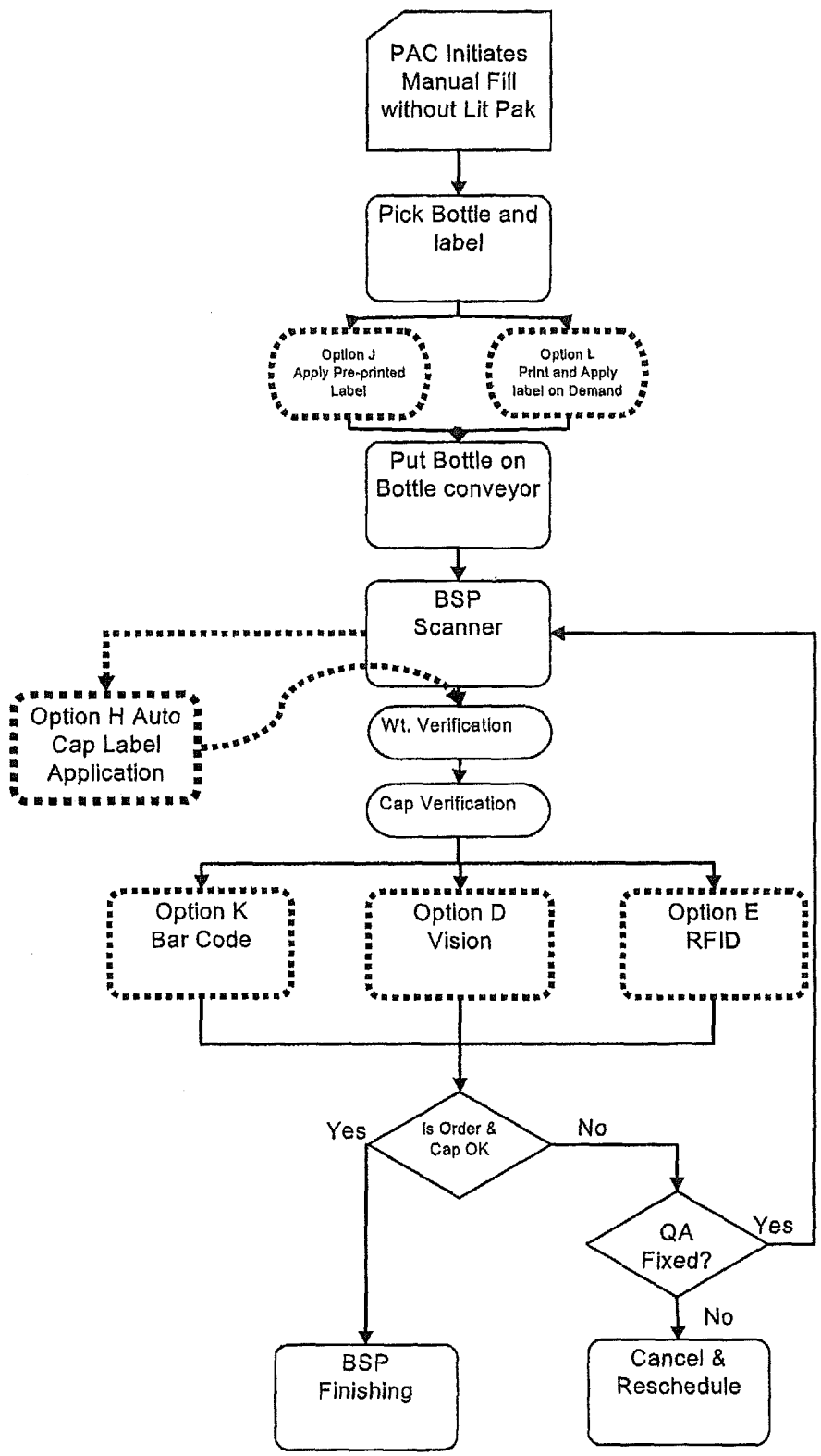

A pre-pack option, of some embodiments, is illustrated in FIG. 25 and can be beneficial to pick and place bottles on a conveyor destined for the ADS BSP. This can automate verification of caps, increase the packing automation, and reduce the total handling requirements. In this operation, bottles can be picked and a cap label applied, either pre-printed or printed on demand. Another alternative can be to pick and put on a conveyor, where the bottle bar code can be read and a label automatically printed and applied.

Figure 26:
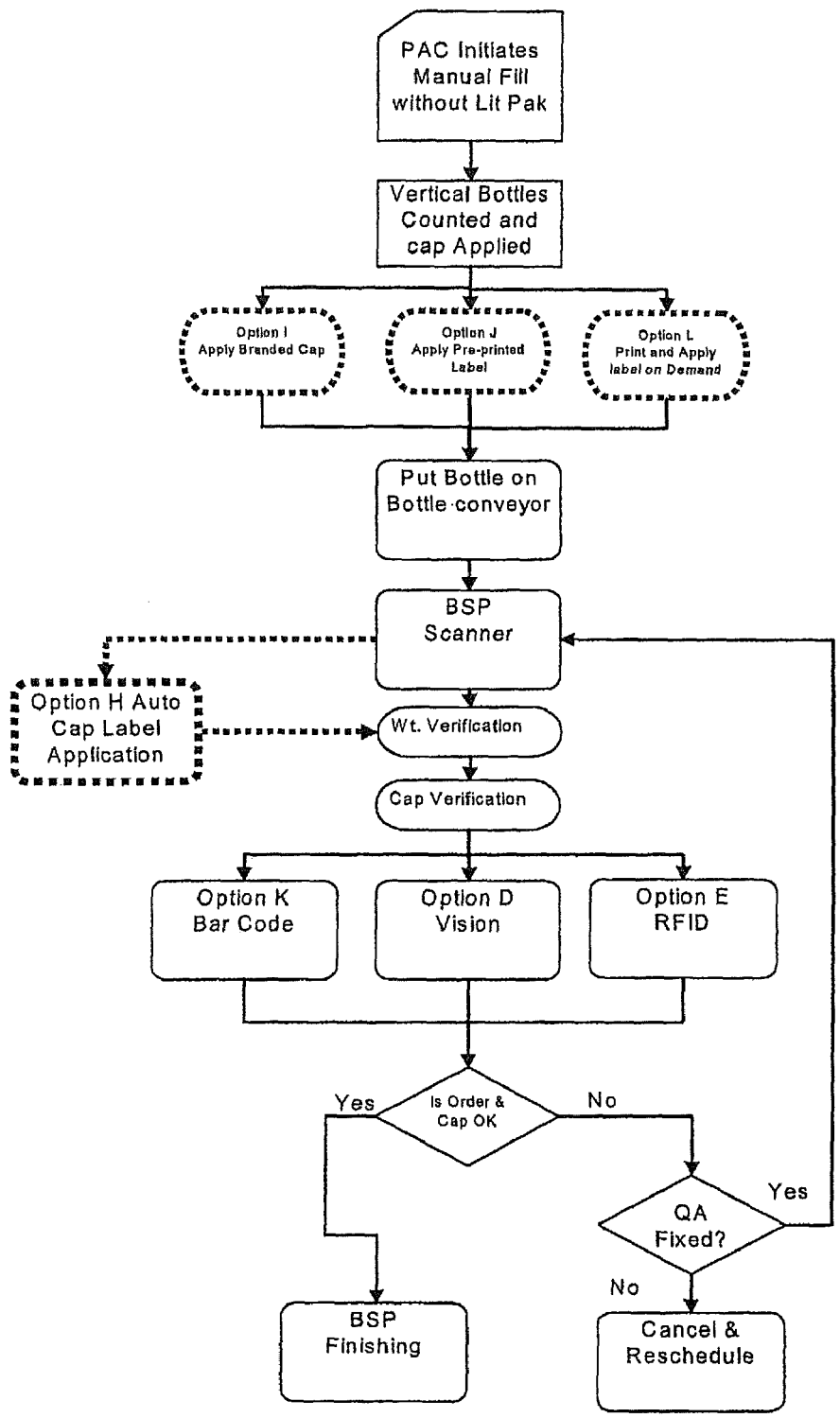

In some embodiments, more vertical volume may be directed to the automated sites if is desired to reduce branding volume in some situations. This alternative would then be the same or similar to the Pre-pack option discussed in reference to FIG. 25, with at least one exception, at 2610, where caps may be labeled at the verticals, through use of a branded cap. This is illustrated in FIG. 26.

Figure 27:
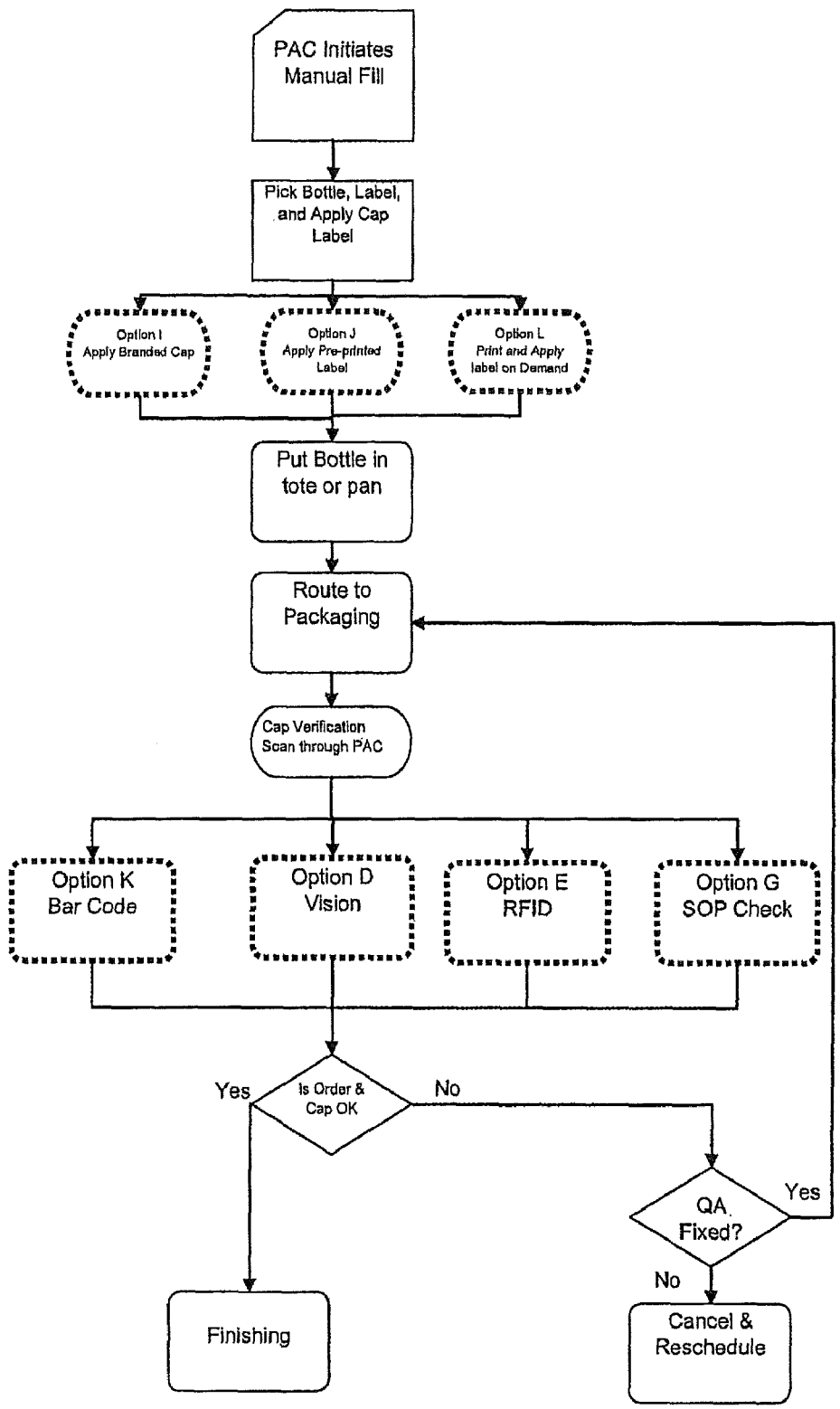

In some embodiments, another option is putting in ADS controls. Several alternatives may be considered, such as, for example, moving all pill count to one of the automated pharmacies, not branding, or applying manually with or without secondary inspection. This is illustrated in FIG. 27.

Figure 28:
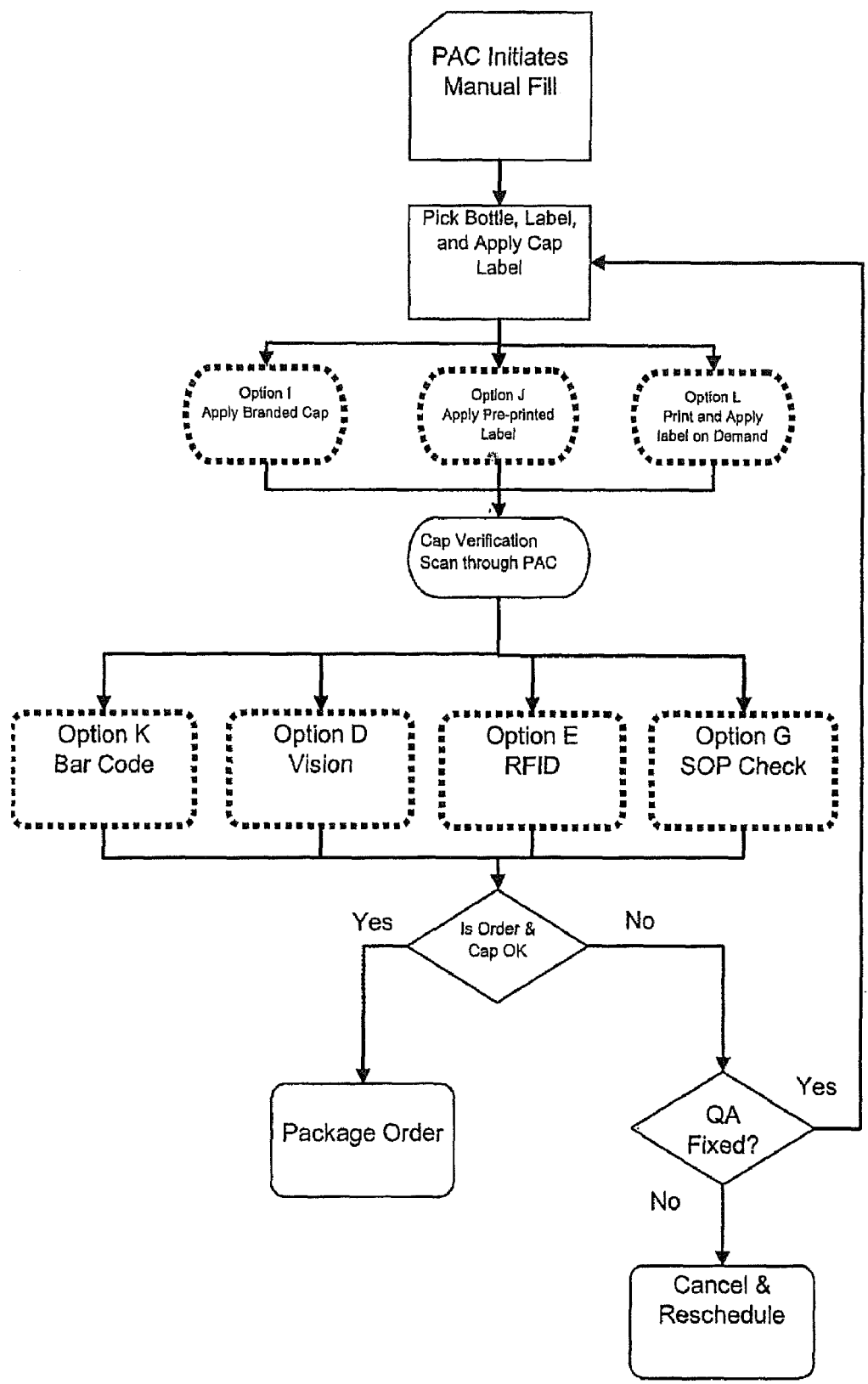

An additional option that can be used, for example, for narcotics is illustrated in FIG. 28. This alternative, for example, is to not brand, or apply manually with or without secondary inspection.

Figure 29:
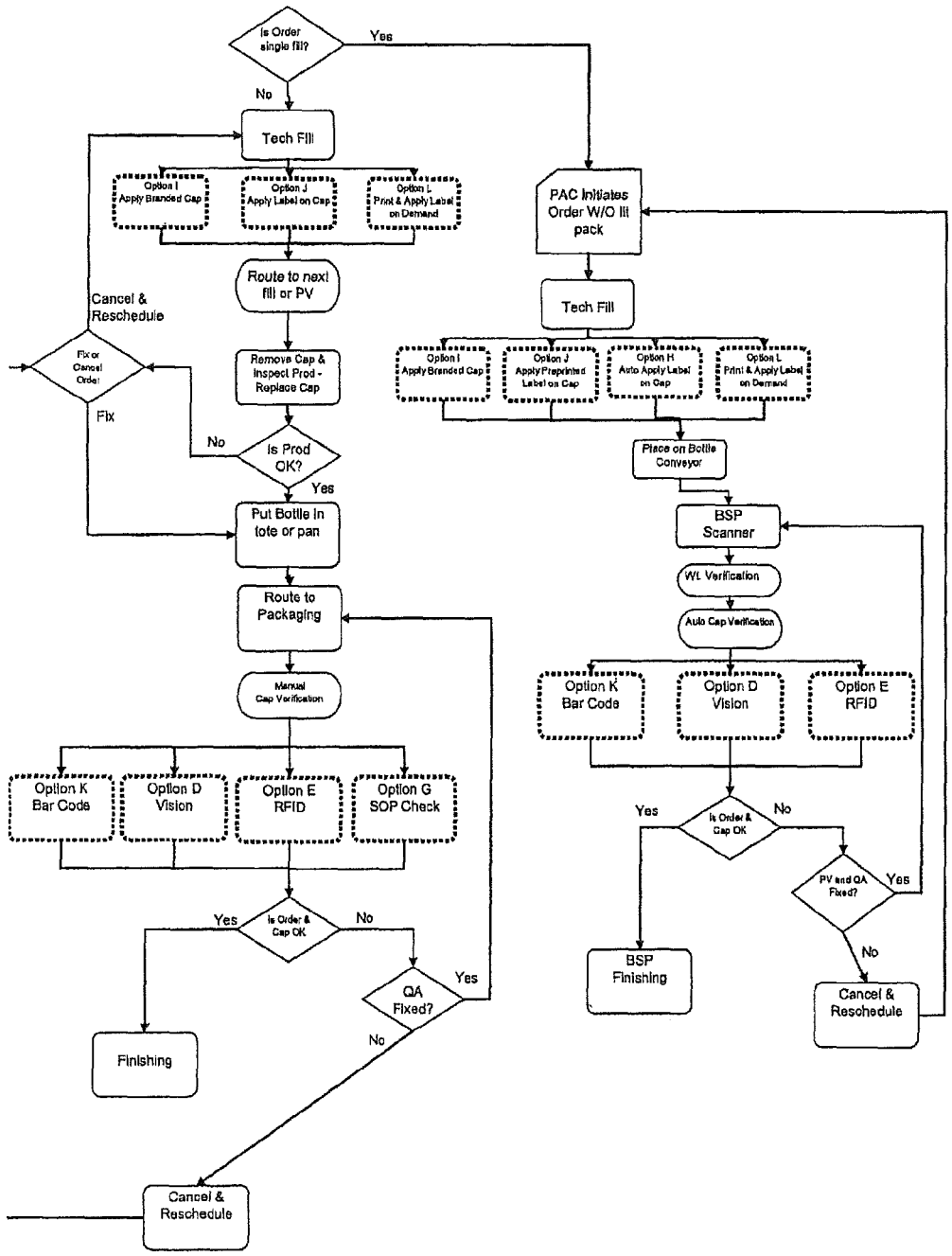
Figure 30:
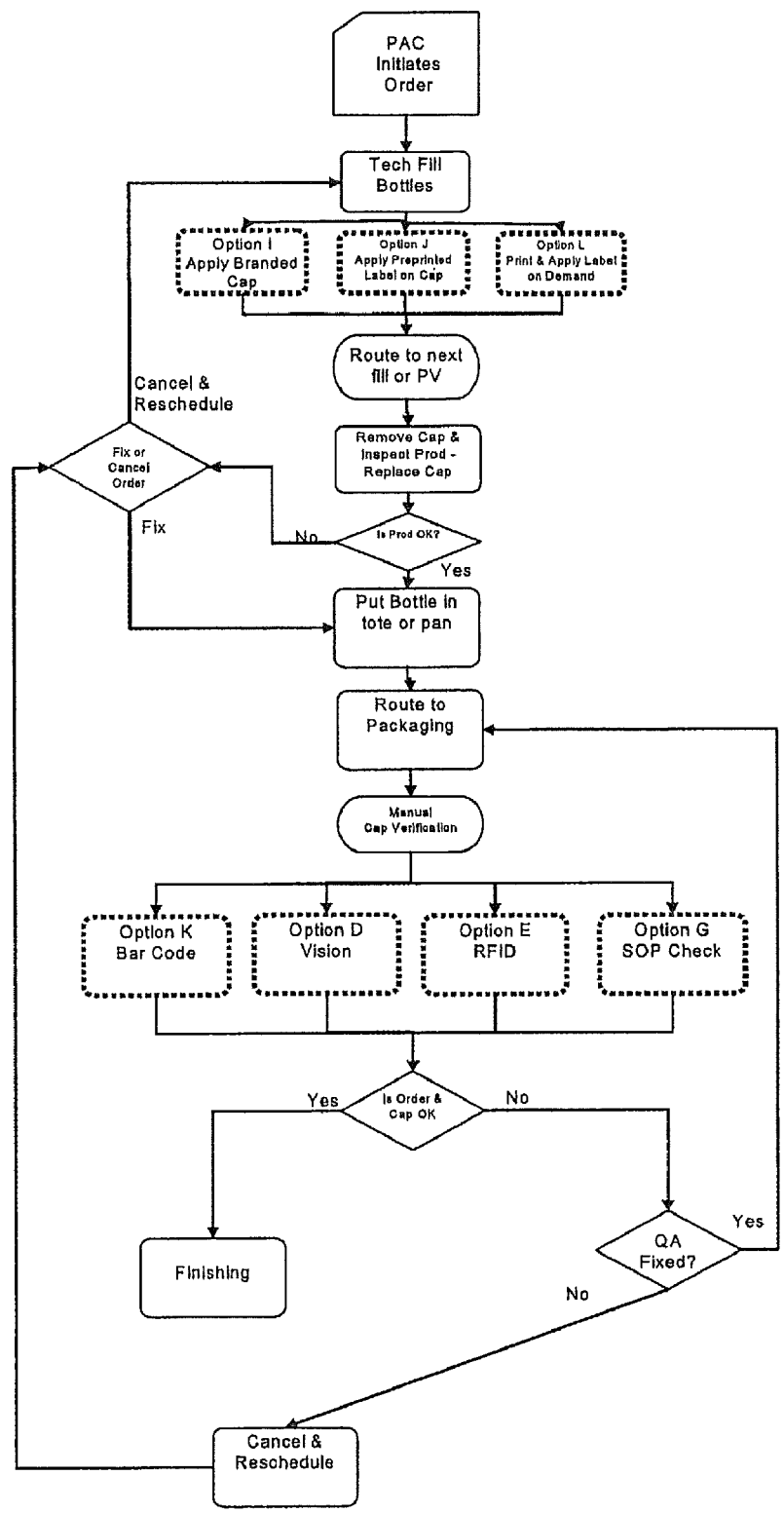

Alternative verification processes, for use in some embodiments, are illustrated in FIGS. 29 and 30. Such embodiments can require cap removal and replacement. A concern is that there can be a potential for mix-up after verification. This may be part of the checking process, matching the label with the cap, however, one typically does not want to slow down the pharmacist performing this function. If the vertical route listed above is selected, these must be filled by a pharmacist, but they may not need product verification. Another option is to select single or only bottle orders, to be picked or filled and routed to BSP. If they require PV, it can be routed to quality assurance, for a Pharmacist to inspect. The cap verification and the packing functions can be automated or manual. This alternative can have the benefit of automation, as well as less tote handling and set-up by support personnel.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

For example, the specific sequence of the above-described process may be altered so that certain processes are conducted in parallel or independent, with other processes, to the extent that the processes are not dependent upon each other. Thus, the specific order of steps described herein are not to be considered implying a specific sequence of steps to perform the above-described process. Other alterations or modifications of the above processes are also contemplated. For example, further insubstantial approximations of the above equations, processes and/or algorithms are also considered within the scope of the processes described herein.

What is claimed is:

1. A system for verifying branding of at least one medication container associated with at least one of a prescription and medication order, comprising:
    a scanning system including at least one scanner for determining the branding of at least one of a first medication container and a cap used to cover the first medication container;
    a transport system that transports the first medication container; and
    a control system that:
        controls the transport system to transport the first medication container to the scanning system; and
        controls the scanning system to determine whether the branding of at least one of the first medication container and the cap correctly matches a predetermined branding among a plurality of brandings based on predetermined criteria.

2. The system of claim 1, wherein the control system further corrects the branding if it is determined that the cap covering the first medication container is not of the predetermined branding.

3. The system of claim 1, wherein the scanning system determines the branding of at least one of the first medication container and the cap covering the first medication container by scanning at least one of at least one barcode, RFID, and text.

4. The system of claim 1, wherein the plurality of possible brandings comprises indicia describing a third party that is responsible for an order associated with the medication container that will be received by at least one member of a pharmaceutical benefits plan.

5. The system of claim 1, wherein the cap used to cover the medication container is at least one of a cover, a lid, a top, a plug, and a stopper.

6. A system for verifying branding of at least one medication container associated with at least one of a prescription and medication order, comprising:

a scanning system including at least one scanner for determining the branding of at least one of a first medication container and a cap used to cover the first medication container;

a transport system that transports the first medication container;

a control system that:
   controls the transport system to transport the first medication container to the scanning system; and
   controls the scanning system to determine whether the branding of at least one of the first medication container and the cap correctly matches a predetermined branding among a plurality of brandings based on predetermined criteria; and a dispensing, capping, and branding system for dispensing, capping, and branding at least one order, wherein the control system further controls the dispensing, capping, and branding system to dispense a medical product into a second medication container, cap the second medication container, and brand the second medication container with a cap of the predetermined branding if it is determined that the cap capped on the first medication container is not of the predetermined branding.

7. The system of claim 6, wherein the capping the second medication container and the branding the second medication container comprise capping the second medication container with a pre-branded cap.

8. A system for verifying branding of at least one medication container associated with at least one of a prescription and medication order, comprising:
   a scanning system including at least one scanner for determining the branding of at least one of a first medication container and a cap used to cover the first medication container;
   a transport system that transports the first medication container;
   a control system that:
      controls the transport system to transport the first medication container to the scanning system; and
      controls the scanning system to determine whether the branding of at least one of the first medication container and the cap correctly matches a predetermined branding among a plurality of brandings based on predetermined criteria; and
   a quality assurance station for correcting the branding using a computer assisted branding system;
   and wherein the control system further controls the transport system to transport the first medication container to the quality assurance station if it is determined that the cap covering the first medication container is not of the predetermined branding and based on whether the quality assurance station can correct the branding.

9. A system for verifying branding of at least one medication container associated with at least one of a prescription and medication order, comprising:
   a scanning system including at least one scanner for determining the branding of at least one of a first medication container and a cap used to cover the first medication container;
   a transport system that transports the first medication container;
   a control system that:
      controls the transport system to transport the first medication container to the scanning system; and
      controls the scanning system to determine whether the branding of at least one of the first medication container and the cap correctly matches a predetermined branding among a plurality of brandings based on predetermined criteria;
   a dispensing, capping, and branding system for dispensing, capping, and branding at least one order; and
   a quality assurance station for correcting the branding of at least one of the first medication container and the cap used to cover the first medication container using a computer assisted branding system, wherein the control system further at least one of:
      controls the transport system to transport the at least one first medication container to the quality assurance station if it is determined the quality assurance station can correct the branding; and
      schedules a new order for the dispensing, capping, and branding system if it is determined the quality assurance station cannot correct the branding.

10. A system for verifying branding of at least one medication container associated with at least one of a prescription and medication order, comprising:
   a scanning system including at least one scanner for determining the branding of at least one of a first medication container and a cap used to cover the first medication container;
   a transport system that transports the first medication container;
   a control system that:
      controls the transport system to transport the first medication container to the scanning system; and
      controls the scanning system to determine whether the branding of at least one of the first medication container and the cap correctly matches a predetermined branding among a plurality of brandings based on predetermined criteria; and
   wherein a carrier holding a plurality of containers holds the first medication container, wherein the at least one scanner comprises a vision system and wherein the control system that determines whether the cap covering the first medication container is of the predetermined branding comprises comparing an image of the first medication container to a location corresponding to the first medication container in a map of the predetermined brandings for the plurality of containers held in the container holding the plurality of containers.

11. A method for verifying the branding of at least one medication container associated with at least one of a prescription and medication order, comprising:
   transporting a first medication container to a scanning system; and
   scanning at least one of the first medication container and a cap used to cover the first medication container at the scanning system to determine whether a branding of at least one of the first medication container and the cap used to cover the first medication container correctly matches a predetermined branding among a plurality of brandings based on predetermined criteria.

12. The method of claim 11, further comprising correcting the branding if it is determined that the cap covering the first medication container is not of the predetermined branding.

13. The method of claim 11, wherein the scanning system determines the branding of at least one of the first medication container and the cap covering the first medication container by scanning at least one of at least one barcode, RFID, and text.

14. The method of claim 11, wherein the plurality of possible brandings comprise at least two of graphics, third-party information, text, and blank caps.

15. The method of claim 11, wherein the plurality of possible brandings comprises indicia describing a third party that is responsible for an order associated with the medication container that will be received by at least one member of a pharmaceutical benefits plan.

16. The method of claim 11, wherein the cap used to cover the medication container is at least one of a cover, a lid, a top, a plug, and a stopper.

17. A method for verifying the branding of at least one medication container associated with at least one of a prescription and medication order, comprising:
    transporting a first medication container to a scanning system; and
    scanning at least one of the first medication container and a cap used to cover the first medication container at the scanning system to determine whether a branding of at least one of the first medication container and the cap used to cover the first medication container correctly matches a predetermined branding among a plurality of brandings based on predetermined criteria, wherein:
    if it is determined that the cap covering the first medication container is not of the predetermined branding:
        dispensing a medical product into a second medication container;
        capping the second medication container; and
        branding the second medication container with a cap of the predetermined branding.

18. The method of claim 17, wherein the capping the second medication container and the branding the second medication container comprise capping the second medication container with a pre-branded cap.

19. A method for verifying the branding of at least one medication container associated with at least one of a prescription and medication order, comprising:
    transporting a first medication container to a scanning system;
    scanning at least one of the first medication container and a cap used to cover the first medication container at the scanning system to determine whether a branding of at least one of the first medication container and the cap used to cover the first medication container correctly matches a predetermined branding among a plurality of brandings based on predetermined criteria; and
    transporting the first medication container to a quality assurance station if it is determined that the cap covering the first medication container is not of the predetermined branding and based on whether the quality assurance station can correct the branding.

20. A method for verifying the branding of at least one medication container associated with at least one of a prescription and medication order, comprising:
    transporting a first medication container to a scanning system; and
    scanning at least one of the first medication container and a cap used to cover the first medication container at the scanning system to determine whether a branding of at least one of the first medication container and the cap used to cover the first medication container correctly matches a predetermined branding among a plurality of brandings based on predetermined criteria; and
    transporting the first medication container to a quality assurance station if it is determined the quality assurance station can correct the branding; or scheduling a new order for a dispensing, capping, and branding system if it is determined the manual quality assurance station cannot correct the branding.

21. A method for verifying the branding of at least one medication container associated with at least one of a prescription and medication order, comprising:
    transporting a first medication container to a scanning system; and
    scanning at least one of the first medication container and a cap used to cover the first medication container at the scanning system to determine whether a branding of at least one of the first medication container and the cap used to cover the first medication container correctly matches a predetermined branding among a plurality of brandings based on predetermined criteria; wherein
    a carrier holding a plurality of containers holds the first medication container, and wherein
    the scanning comprises using a vision system, and
    further comprising comparing an image of the first medication container to a location corresponding to the first medication container in a map of the predetermined brandings for the plurality of containers held in the container holding the plurality of containers.

22. A method for verifying the branding of at least one medication container associated with at least one of a prescription and medication order, comprising:
    dispensing a medical product into a first medication container;
    capping the first medication container;
    branding the first medication container with a predetermined branding among a plurality of brandings based on predetermined criteria;
    transporting a first medication container to a scanning system; and
    scanning at least one of the first medication container and a cap used to cover the first medication container at the scanning system to determine whether a branding of at least one of the first medication container and the cap used to cover the first medication container correctly matches a predetermined branding among a plurality of brandings based on predetermined criteria.

23. The method of claim 22, wherein the branding the first medication container includes branding at least one of the body of the first medication container and a cap of the first medication container.

* * * * *